(12) United States Patent
Riman et al.

(10) Patent No.: US 7,998,219 B2
(45) Date of Patent: Aug. 16, 2011

(54) HYDROXYAPATITE WITH CONTROLLABLE SIZE AND MORPHOLOGY

(75) Inventors: Richard E. Riman, Belle Mead, NJ (US); Alexander Burukhin, Moscow (RU); Eugene Zlotnikov, Highland Park, NJ (US); Dan Haders, Somerset, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 361 days.

(21) Appl. No.: 11/813,368

(22) PCT Filed: Dec. 21, 2005

(86) PCT No.: PCT/US2005/046209
§ 371 (c)(1),
(2), (4) Date: Jul. 5, 2007

(87) PCT Pub. No.: WO2006/083418
PCT Pub. Date: Aug. 10, 2006

(65) Prior Publication Data
US 2008/0206554 A1    Aug. 28, 2008

Related U.S. Application Data

(60) Provisional application No. 60/641,083, filed on Jan. 4, 2005.

(51) Int. Cl.
B05D 3/00 (2006.01)
C01B 25/32 (2006.01)
A61F 2/28 (2006.01)
B01J 27/18 (2006.01)

(52) U.S. Cl. ........ 623/23.56; 73/1.06; 106/35; 106/462; 210/656; 423/308; 427/2.27; 427/430.1; 427/435; 427/443.2

(58) Field of Classification Search .................. 423/308, 423/309, 311; 427/2.27, 430.1, 435, 443.2; 428/221, 402; 106/35, 462; 623/23.56; 516/1, 516/922; 502/208; 210/656; 73/1.06
See application file for complete search history.

(56) References Cited

U.S. PATENT DOCUMENTS

| | | | |
|---|---|---|---|
| 4,097,935 A | | 7/1978 | Jarcho |
| 4,429,691 A | * | 2/1984 | Niwa et al. ............... 606/77 |
| 5,073,410 A | * | 12/1991 | Paz-Pujalt .............. 427/226 |
| 5,128,169 A | * | 7/1992 | Saita et al. .............. 427/2.27 |
| 5,405,436 A | * | 4/1995 | Maurer et al. ............ 106/35 |
| 5,427,754 A | * | 6/1995 | Nagata et al. ........... 423/308 |
| 5,830,480 A | | 11/1998 | Ducheyne et al. |

(Continued)

FOREIGN PATENT DOCUMENTS

JP    06245992    9/1994

(Continued)

OTHER PUBLICATIONS

Bertoni et al., "Nanocrystals of magnesium and fluoride susbtituted hydroxypatite", J. Inorg. Biochem., 72 (1):29-35 (1998).

(Continued)

Primary Examiner — Wayne Langel
(74) Attorney, Agent, or Firm — Fox Rothschild LLP

(57) ABSTRACT

A ceramic powder of non-agglomerated non-aggregated phase-pure hydroxyapatite having a controllable morphology. Also presented is a film of phasepure crystalline hydroxyapatite grains having a controllable morphology. Methods for preparing the same are also provided.

43 Claims, 18 Drawing Sheets

Characteristics of hydroxyapatite powders

| Morphological Type of Hydroxyapatite | Crystals Length (diameter) microns | Aspect ratio |
|---|---|---|
| Hexagonal rods | 3-5 | 5 |
| Hexagonal rods | ~30 | 4-5 |
| Barrels | 1-2 | ~2 |
| Tubular | 3-5 | 3 |
| Spheres | 0.5-1 | 1 |
| Platelets | 1-2 | 0.7 |

U.S. PATENT DOCUMENTS

| | | | | |
|---|---|---|---|---|
| 5,858,318 A * | 1/1999 | Luo | | 423/308 |
| 6,013,591 A * | 1/2000 | Ying et al. | | 501/1 |
| 6,027,742 A | 2/2000 | Lee et al. | | |
| 6,153,266 A * | 11/2000 | Yokogawa et al. | | 427/419.1 |
| 6,344,061 B1 * | 2/2002 | Leitao et al. | | 623/23.5 |
| 6,426,114 B1 * | 7/2002 | Troczynski et al. | | 427/2.27 |
| 6,569,489 B1 * | 5/2003 | Li | | 427/2.26 |
| 6,720,023 B1 * | 4/2004 | Kim et al. | | 427/2.27 |
| 6,777,214 B1 * | 8/2004 | Yamashita | | 435/173.1 |
| 7,008,450 B2 * | 3/2006 | Kim et al. | | 623/11.11 |
| 7,247,288 B2 * | 7/2007 | Kumta et al. | | 423/308 |
| 7,390,335 B2 * | 6/2008 | Chow | | 23/293 A |
| 7,527,687 B2 * | 5/2009 | Genge et al. | | 106/690 |
| 2003/0219466 A1 * | 11/2003 | Kumta et al. | | 424/423 |
| 2004/0034141 A1 | 2/2004 | Aramaki et al. | | |
| 2005/0226939 A1 * | 10/2005 | Ramalingam et al. | | 424/602 |
| 2006/0062925 A1 * | 3/2006 | Rohanizadeh et al. | | 427/430.1 |
| 2008/0220148 A1 * | 9/2008 | Clarkson et al. | | 427/2.27 |

FOREIGN PATENT DOCUMENTS

| | | |
|---|---|---|
| WO | 97/17285 A1 | 5/1997 |
| WO | 99/32400 A1 | 7/1999 |
| WO | 00/03747 A2 | 1/2000 |
| WO | 03000588 | 1/2003 |

OTHER PUBLICATIONS

Bigi et al., "Magnesium Influence on hydroxypatite crystalization", J. Inorg. Biochem. 49, 69-78 (1993).

Patel, P.N., "Magnesium Calcium Hydroxylapatite Solid Solutions", J. Inorg. Nucl. Chem, vol. 42, pp. 1129-1132 (1980).

Yasukawa, A. et al., "Prepararion and characterization of magnesium-calcium hydroxyapatites", J. Mater. Chem, vol. 6, No. 8, pp. 1401-1405 (1996).

Liao, J. et al., "Synthesis of Ca-Mg Apatite via a Mechanochemical Hydrothermal Process", J. Mater. Synth. Process, vol. 8, No. 5/6, pp. 305-311 (2000).

Yokogawa, Y. et al., "Synthesis of Calcium-Strontium, Calcium-Magnesium, Magnesium-Strontium Apatite Through Mechanochemical Method", Report of National Industrial Research Institute of Nagoya, vol. 45, No. 4, pp. 161-166 (1996).

Riman et al., "Solution synthesis of hydroxyapatite designer particulates," Solid State Ionics 151 (2002); pp. 393-402.

Lopatin et al., "Ion-beam densification of hydroxyapatite thin films," Nucl. Instr. and Meth. in Phys. Res. B 145 (1998); pp. 522-531.

Kothapalli et al., "Influence of temperature and concentration on the sintering behavior and mechanical properties of hydroxyapatite," Acta Materialia 52 (2004); pp. 5655-5663.

Furukawa et al., "Biodegradation behavior of ultra-high-strength hydroxyapatite/poly (L-lactide) composite rods for internal fixation of bone fractures," Biomaterials 21 (2000); pp. 889-898.

Furuzono et al., "Nano-scaled hydroxyapatite/polymer compostie IV. fabrication and cell adhesion properties of a three-dimensional scaffold made of composite material with a silk fibroin substrate to develop a percutaneous devices," J Artif Organs (2004) 7: pp. 137-144.

European Search Report issued for EP Application No. 05854856.1.

* cited by examiner

Figure 1. Characteristics of hydroxyapatite powders

| Morphological Type of Hydroxyapatite | Crystals Length (diameter) microns | Aspect ratio |
|---|---|---|
| Hexagonal rods | 3-5 | 5 |
| Hexagonal rods | ~30 | 4-5 |
| Barrels | 1-2 | ~2 |
| Tubular | 3-5 | 3 |
| Spheres | 0.5-1 | 1 |
| Platelets | 1-2 | 0.7 |

Figure 2. Conditions of the Syntheses (Hexagonal, Spherical, Tubular, Barrels, and Platelets)

| # | Calcium Nitrate m | Tri-ethyl Phosphate m | Ethylendiamine tetracetic acid m | Ammonia m | Potassium Hydroxide m | Time h | Temperature °C | Rotation speed (rpm) |
|---|---|---|---|---|---|---|---|---|
| 1 | 0.5 | 0.2015 | 0.5 | 0 | 2 | 24 | 200 | 0 |
| 2 | 0.05 | 0.02015 | 0.025 | 20 | 0.2 | 25 | 200 | 0 |
| 3 | 0.5 | 0.2015 | 0 | 0 | 2 | 24 | 200 | 300 |
| 4 | 0.5 | 0.25 | 0 | 2 | 0 | 24 | 200 | 200 |
| 5 | 0.5 | 0.2015 | 0 | 2 | 0 | 24 | 200 | 1200 |
| 6 | 0.5 | 0.2015 | 0 | 0 | 2 | 24 | 180 | 0 |
| 7 | 0.15 | 0.07 | 0.15 | 0 | 0.7 | 20 | 180 | 0 |

Figure 3. Hydroxyapatite Coating

| # | Calcium Nitrate m | Tri-ethyl Phosphate m | Ethylendiamine tetracetic acid m | Ammonia m | Potassium Hydroxide m | Time h | Temperature °C | Rotation speed | Substrate |
|---|---|---|---|---|---|---|---|---|---|
| 7 | 0.25 | 0.2015 | 0.25 | 0 | 2 | 24 | 200 | 0 | Ti-foil 0.127 mm (Aldrich) |
| 8 | 0.25 | 0.2015 | 0.25 | 0 | 2 | 24 | 200 | 0 | Stainless Steel 304 |
| 9 | 0.25 | 0.2015 | 0.25 | 0 | 2 | 24 | 200 | 0 | Sapphire |
| 10 | 0.25 | 0.2015 | 0.25 | 0 | 2 | 24 | 184 | 0 | Yttria |
| 11 | 0.25 | 0.2015 | 0.25 | 0 | 2 | 24 | 200 | 0 | Teflon |
| 12 | 0.25 | 0.2015 | 0.25 | 0 | 2 | 24 | 200 | 0 | Titanium sponge (McMaster) |
| 13* | | | 0.25 | 0 | 2 | 18.5 | 200 | 0 | Stainless Steel 316 |
| 14* | | | 0.25 | 0 | 2 | 27 | 200 | 0 | Titanium alloy Ti 4Al-4V F136 |
| 15* | | | 0.25 | 0 | 2 | 27 | 200 | 0 | Titanium Alloy Ti 4Al-4V F136 B348 |
| 16* | | | 0.25 | 0 | 2 | 18 | 200 | 0 | Cobalt Chrome Alloy F75 |
| 17 | 0.25 | 0.2 | 0 | 2 | 0 | 6 | 180 | 200 | Titanium wire (McMaster) diameter 0.25 mm |

*The substrate was sanded with 320 grit sand paper.
Coatings are illustrated with the microphotographs in figures 7-8

Figure 10. Conditions for controlling synthesis of hexagonal hydroxyapatite particles

| Temperature °C | Time Hours | EDTA g | Ca(NO$_3$)$_2$*4 H$_2$O g | TEP g | KOH | Water | Aspect Ratio | Length microns |
|---|---|---|---|---|---|---|---|---|
| 200 | 20 | 4.38 | 3.54 | 2.20 | 6.72 | 43.15 | 1.33 | 2.23 |
| 200 | 20 | 1.58 | 2.13 | 1.32 | 4.03 | 50.94 | 1.70 | 10.22 |
| 200 | 40 | 4.38 | 3.54 | 2.20 | 6.72 | 43.15 | 2.05 | 18.17 |
| 200 | 40 | 1.58 | 2.13 | 1.32 | 4.03 | 50.94 | 1.84 | 13.94 |
| 180 | 20 | 4.38 | 3.54 | 2.20 | 6.72 | 43.15 | 0.74 | 2.88 |
| 180 | 20 | 1.58 | 2.13 | 1.32 | 4.03 | 50.94 | 0.58 | 1.53 |
| 180 | 40 | 4.38 | 3.54 | 2.20 | 6.72 | 43.15 | 1.04 | 5.26 |
| 180 | 40 | 1.58 | 2.13 | 1.32 | 4.03 | 50.94 | 1.56 | 7.66 |

ODF project:
G:\Daniel\Pole\14hrR002.rw1
Pole figure:    001 Raw
Intensities:

|     | Psi  | Phi   | Intensity |
|-----|------|-------|-----------|
| Min | 90.0 | 34.5  | 213.160   |
| Max | 5.0  | 126.5 | 10322.560 |

Dimension:  2.5D
Scale:      Linear
Grid settings:

|       | Psi | Phi |
|-------|-----|-----|
| First | 0   | 0   |
| Last  | 90  | 360 |
| Step  | 30  | 90  |

ODF project:
G:\Daniel\Pole\26hrR002.rw1
Pole figure: 001 Raw
Intensities:

|  | Psi | Phi | Intensity |
|---|---|---|---|
| Min | 90.0 | 269.5 | 228.010 |
| Max | 1.0 | 49.5 | 13133.160 |

Dimension: 2.5D
Scale: Linear
Grid settings:

|  | Psi | Phi |
|---|---|---|
| First | 0 | 0 |
| Last | 90 | 360 |
| Step | 30 | 90 |

HYDROXYAPATITE WITH CONTROLLABLE SIZE AND MORPHOLOGY

CROSS-REFERENCE TO RELATED APPLICATIONS

This application claims priority under 35 U.S.C. §119(e) to U.S. Provisional Application Ser. No. 60/641,083, which was filed on Jan. 4, 2005; and U.S. Provisional Application Ser. No. 60/636,973, which was filed on Dec. 20, 2004. The disclosures of both applications are incorporated herein by reference.

BACKGROUND OF THE INVENTION

Hydroxyapatite (HAp, chemical formula $Ca_{10}(PO_4)_6(OH)_2$) has attracted the attention of researchers over the past thirty years as an implant material because of its excellent biocompatibility and bioactivity. HAp has been extensively used in medicine for implant fabrication. It is commonly the material of choice for the fabrication of dense and porous bioceramics. Its general uses include biocompatible phase-reinforcement in composites, coatings on metal implants and granular fill for direct incorporation into human tissue. It has also been extensively investigated for non-medical applications such as a packing material/support for column chromatography, gas sensors and catalysts, as a host material for lasers, and as a plant growth substrate.

Previously explored methods of hydroxyapatite synthesis for particles include conventional solid-state reactions, sol-gel, phase transformation, hydrothermal, chemical precipitation, and precipitation in simulated body fluid. Solid-state reactions utilize high temperature processes (600-1250° C.) using powders of compounds such as tricalcium phosphate and calcium hydroxide. The product of the high temperature reaction is communited to a powder of a desired size range. However, materials made with this approach do not have controlled morphology. Further, they have broad size distributions and wear of the milling media and container introduces impurities. Sol-gel reactions require a sintering step to obtain crystalline product, which is not always phase-pure. A similar downfall is seen with phase transformation—the product is rarely phase-pure and does not have controllable size or morphology. Aqueous precipitation methods have been widely used, but generally either produce fiber morphologies or large agglomerates of nanostructured particles with no well-defined morphology. Simulated body fluid syntheses have not been demonstrated to make particles with controlled size and morphology and have a very low process yields, making them impractical for manufacturing.

Various morphological types of hydroxyapatite have been disclosed in patent literature. For example, U.S. Pat. No. 5,227,147 claims the production of whiskers i.e. fibers with aspect ratio above 10 for biomedical applications. The length of the whiskers according to this invention varies from 1 to 1000 microns.

A hydrothermal process for the preparation of plate-like hexagonal hydroxyapatite particles in the presence of water-miscible organic solvents is described in U.S. Pat. No. 5,427,754. The size (maximum diameter) of hydroxyapatite platelets obtained according to this invention generally falls between 50 and 200 nm.

U.S. Pat. No. 6,358,532 reveals a sol-gel method of microbead formation. The microbeads have a diameter of 0.1-6 mm and a wall thickness from 20 to 230 microns.

U.S. Pat. No. 4,335,086 describes the preparation of hydroxyapatite by heating an aqueous suspension of brushite to prepare rosette-shaped crystals. These crystals are between 40 and 70 microns in size.

Further, there are numerous patents related to production and application of spherical hydroxyapatite particles. For example, U.S. Pat. No. 5,082,566 describes a calcium-phosphate type hydroxyapatite from 0.5 to 50 microns in diameter. Hydroxyapatite is produced by spray-drying a gel or slurry form of an aqueous calcium phosphate solution into a high-temperature air stream ranging from 100-200° C. This instantaneously dries the granular apatite, which is then fired at 400-700° C.

U.S. Pat. Nos. 5,108,956 and 5,205,928 describe processes for preparing sintered microspherical hydroxyapatite particles by spray-firing a suspension of hydroxyapatite dispersed in an inflammable solvent.

The application of spherical hydroxyapatite particles of 10-100 microns in diameter as a filler for biodegradable polymers (U.S. Pat. No. 5,766,618) or an ingredient of an injectable composition (U.S. Pat. No. 5,922,025) have been speculated, but with no specific details on the production of the particles available.

Spherical hydroxyapatite aggregates (1-10 microns) built of about 0.1 micron crystals are described in U.S. Pat. No. 4,874,511 as an adsorbent for chromatograph columns. 5 mm long hydroxyapatite filaments with diameter not greater than 5 microns are disclosed in U.S. Pat. No. 5,652,056.

Spherical hydroxyapatite crystals are described in U.S. Pat. No. 6,013,591. The particles of 20-150 nm in size were sintered by pressurizing and calcination. Hollow spheres and doughnuts are disclosed in U.S. Pat. No. 5,858,318 with sizes from 1 to 8 microns.

Coatings of hydroxyapatite find use in many applications, such as, for example, biomedical devices (prosthesis, implants), protection of metal surfaces against corrosion, aggressive chemicals and environment, and strengthening of the various surfaces. The properties of hydroxyapatite depend, to a great extent, on the size and shape of the particles. Therefore, the morphology of the particles is extremely important for production of high quality coatings. However, numerous patents related to coatings are not directed to the morphology and size of hydroxyapatite particles.

U.S. Pat. No. 6,426,114 discloses a ceramic coating with a thickness of 1-5 microns made by a sol-gel method at relatively low temperature (350° C.).

U.S. Pat. No. 4,871,578 discloses the hydroxyapatite coating of metal and ceramic surfaces made by coating a substrate with tri-calcium phosphate and the subsequent transformation of this phase into hydroxyapatite by interaction with water at elevated temperature.

U.S. Pat. Nos. 4,794,023 and 4,960,646 disclose the coating of a metal substrate (titanium, titanium alloys, and stainless steel) by treatment with a nitric acid solution containing dissolved hydroxyapatite. After drying, the substrate undergoes fire treatment at 300° C., which turns the coating into hydroxyapatite. An essentially similar method is disclosed in U.S. Pat. No. 5,128,169. This patent recites metal, ceramic, and glass as possible substrates. Particles of hydroxyapatite constituting a coating have ranges from 0.1 to 1 micron.

U.S. Pat. No. 5,128,146 discloses the plasma spray coating of titanium and ceramic substrates with hydroxyapatite particles of 10 to 30 microns in diameter.

U.S. Pat. Nos. 5,164,187 and 5,279,831 disclose the solution treatment of a metal substrate that coats it with a multi-layered film of hydroxyapatite made of whiskers 1-40 microns long and 0.01-20 microns in diameter. In order to control the size of hydroxyapatite crystals, these patents change the concentration of the precursor.

U.S. Pat. No. 5,609,633 recites a hydroxyapatite coating of titanium or titanium alloys in an alkaline media comprising an inner layer of amorphous titanate and an outer layer of crystalline hydroxyapatite. The thickness of the layers varies from 0.1 to 10 microns for the inner layer and above 1 micron for the outer layer.

U.S. Pat. No. 5,676,997 discloses the coating process with a precursor having salts with phosphoric acid and calcium in the presence of chelating agents, in particular, ethylenediaminetetraacetic acid with no specification of the hydroxyapatite morphology produced.

U.S. Pat. No. 5,676,997 discloses the use of ethylendiaminetetracetic acid and other chelating agents to control the synthesis of hydroxyapatite on metal substrates. According to this patent the synthesis/coating process includes the preparation of a homogeneous precursor, submerging the substrate into the precursor, and drying the precursor solution on the substrate. Thus, this method totally excludes the possibility of homogeneous nucleation of hydroxyapatite.

Degradable components as a source of phosphate are described in U.S. Pat. No. 6,426,114. The patent discloses the use of hydrolysable tri-ethyl phosphite in a sol-gel process and includes a calcination step. Another disadvantage of this method is the immiscibility of tri-ethyl phosphite with water, even in presence of organic solvents such as ethyl alcohol.

The use of water miscible tri-ethyl phosphate is described by H. K. Varma, S. N. Kalkura and R. Sivakumar in Ceramics International. 24 (1998), p. 467. The synthesis of hydroxyapatite according to this publication includes dissolution of calcium nitrate in tri-ethyl phosphate with further heating to 500° C. At this temperature, the degradation of tri-ethyl phosphate takes place with the formation of tri-calcium phosphate. Further calcination of tri-calcium phosphate leads to the formation of hydroxyapatite or a mixture of tri-calcium phosphate with hydroxyapatite. The final product has no controllable morphology and, according to XRD data, is contaminated with tri-calcium phosphate and/or calcium oxide.

Therefore, the need exists for hydroxyapatite having a controllable morphology and methods for producing the same.

SUMMARY OF THE INVENTION

This need is met by the present invention.

There is provided, in accordance with the present invention, a film of phase-pure crystalline hydroxyapatite grains having a controllable morphology. Also provided is a ceramic powder of non-agglomerated non-aggregated phase-pure hydroxyapatite having a controllable morphology.

The controllable morphologies include hexagons with a length from about 50 nm to about 5000 nm and an aspect ratio from about 0.5 to about 5; spheres made of hexagonal primary particles and having a secondary particle size from about 50 nm to about 5000 nm; tubular particles with a length from about 50 nm to about 5000 nm with an aspect ratio from about 0.5 nm to about 5 nm; barrel-shaped particles with a length from about 50 nm to about 5000 nm with aspect ratio from about 0.5 to about 5.0; and mixtures thereof.

In one embodiment, the film passivates the surface of a substrate selected from metals, metal oxides, alloys, and polymers stable in alkaline media at elevated temperature. In another embodiment, the metal is titanium. In yet another embodiment, the alloy is mild steel, stainless steel, cobalt/chrome, or a titanium alloy. In a further embodiment, the polymer stable in alkaline media at elevated temperature is fluoropolymers, polyvinylchloride, or polyethylene terephtalate.

In one embodiment, the substrate is selected from porous substrates, wire meshes, wires, rods, bars, ingots, sheets, and free-form shapes. In another embodiment, the substrate is selected from titanium, steel, stainless steel, and cobalt-chrome.

In yet another embodiment, the crystalline hydroxyapatite grains are oriented in a similar direction on the substrate. In a further embodiment, the crystalline hydroxyapatite grains have varying lengths.

In one embodiment, the texture of the film is smooth or rough.

In another embodiment, the morphology is hexagonal and the substrate is a sapphire single crystal. In yet another embodiment, the morphology is cube-shaped and the substrate is zirconia.

In one embodiment, a method for producing a phase-pure hydroxyapatite includes dissolving a source of calcium ions, a source of hydroxide ions, and an organophosphate in a common solvent; and heating the solution at a temperature less than 300° C., so that the organophosphate hydrolyzes to form $PO_4^{3-}$ ions that react with said calcium and hydroxide ion sources to form hydroxyapatite of uniform size and morphology.

In another embodiment, the calcium ion source contains calcium ions bound to a chelating agent. In yet another embodiment, the chelating agent is ethylendiamine tetracetic acid (EDTA).

In a further embodiment, the solvent comprises water; and the hydroxide ion source comprises ammonia.

In an additional embodiment, a method for producing a phase-pure hydroxyapatite film on a substrate includes dissolving a chelated source of calcium ions, a source of hydroxide ions, and an organophosphate in a common solvent; placing a substrate into the solution; and heating the solution at a temperature less than 300° C., so that the organophosphate hydrolyzes to form $PO_4^{3-}$ ions that react with said calcium and hydroxide ion sources to deposit hydroxyapatite on said substrate.

In another embodiment, the organophosphate has a general formula $(RO)_3PO$, wherein R represents hydrogen or an organic hydrocarbon radical hydrolysis derivative of the organophosphate, provided that at least one R is not H.

In an additional embodiment, the solubility of the organophosphate in water is not less than 5% by weight at room temperature. In one embodiment, the organophosphate is miscible with water at room temperature.

In another embodiment, the calcium ions are chelated to a chelating agent selected from ethylene diaminetetracetic acid, a salt thereof, and mixtures thereof.

Another embodiment further includes controlling the texture of the film.

In one embodiment, the substrate is selected from metals, metal oxides, alloys, and polymers stable in alkaline media at elevated temperatures. In another embodiment, the metal is titanium. In yet another embodiment, the alloy is mild steel, stainless steel, cobalt/chrome, or a titanium alloy.

In one embodiment, the solution is heated in a sealed vessel so that said reaction occurs at autogenous pressure.

In another embodiment, a composite includes a polymer and the ceramic powder. In one embodiment, the polymer is selected from poly-lactic acid, poly glycolic acid, polycaprolactone, copolymers thereof, and mixtures thereof.

Another embodiment includes a packing material for use in a chromatography column or gas sensor or as a catalytic support made with the ceramic powder.

An additional embodiment includes aerosol particles made with the ceramic powder.

Another embodiment includes an extending pigment for paints, coatings, and plastics made with the ceramic powder.

In yet another embodiment, a biocompatible hard tissue implant including the hydroxyapatite film is presented. In one embodiment, the biocompatible hard tissue implant is a metal or polymeric implant coated with said film. In another embodiment, the biocompatible hard tissue implant includes a polymeric composite.

In one embodiment, a granular fill for direct incorporation into human or animal tissues made with the ceramic powder is presented. In another embodiment, the granular fill includes a metal or polymeric composite for filling dental cavities.

In a further embodiment, a dentifrice composition is presented, which includes the ceramic powder.

BRIEF DESCRIPTION OF THE DRAWINGS

FIG. 1 is a table summarizing the characteristics of hydroxyapatite powders;

FIG. 2 is a table summarizing the conditions of the syntheses of exemplary hexagonal, spherical, tubular, barrel, and platelet hydroxyapatite particles;

FIG. 3 is a table summarizing the conditions of the syntheses of hydroxyapatite coatings;

FIG. 10 is a table summarizing conditions for controlling the synthesis of exemplary hexagonal hydroxyapatite particles;

DETAILED DESCRIPTION OF THE INVENTION

The present invention is related to hydroxyapatite particles and coatings having a controllable morphology. Methods of preparing the particles and coatings are also presented.

The ability to produce hydroxyapatite powders and films with controlled physical and chemical characteristics offers tremendous advantages for a wide range of applications suitable for this material. Hydroxyapatite has reported uses for biomedical, chromatographic, and piezoelectric applications. The primary focus has been to make these materials with a high degree of phase purity, that is, materials that possess a low concentration of tricalcium phosphate (TCP) or amorphous calcium phosphate (ACP) because impurities such as these are easily resorbed into aqueous solution.

However, the impact of using hydroxyapatite with a wide range of sizes and morphologies has not been considered. Further, the applicants are unaware of any quantitative assessments of degree of agglomeration or aggregation of hydroxyapatite powder. For film synthesis, methods have been reported that produce dense films, however, no attention was focused on the morphology of the grains in the structure or their specific orientation.

There is a range of morphologies useful in the present invention. For example, hexagonal morphologies, typically found in natural hydroxyapatite found in bone and teeth, are an important because such materials would have similar biological interactions. The present invention demonstrates that novel morphologies based on primary single crystalline particles or polycrystalline particles of controlled secondary morphology based on controlled aggregation of primary particles of controlled morphology is feasible.

Relevant morphologies on primary or secondary hierarchy include spheres, hexagons, tubular, platelets, barrels, and cube-shaped structures. Particles having such morphologies include particles that essentially have the morphologic shape. For example, for particles that are hexagons, the particles need not be perfect hexagons.

Using orthogonal a-b-c axes as a reference frame, several morphologies are defined as follows:

The term "spheres" is used herein to mean equiaxed particles having either a primary or secondary particle structure.

Figure 8:
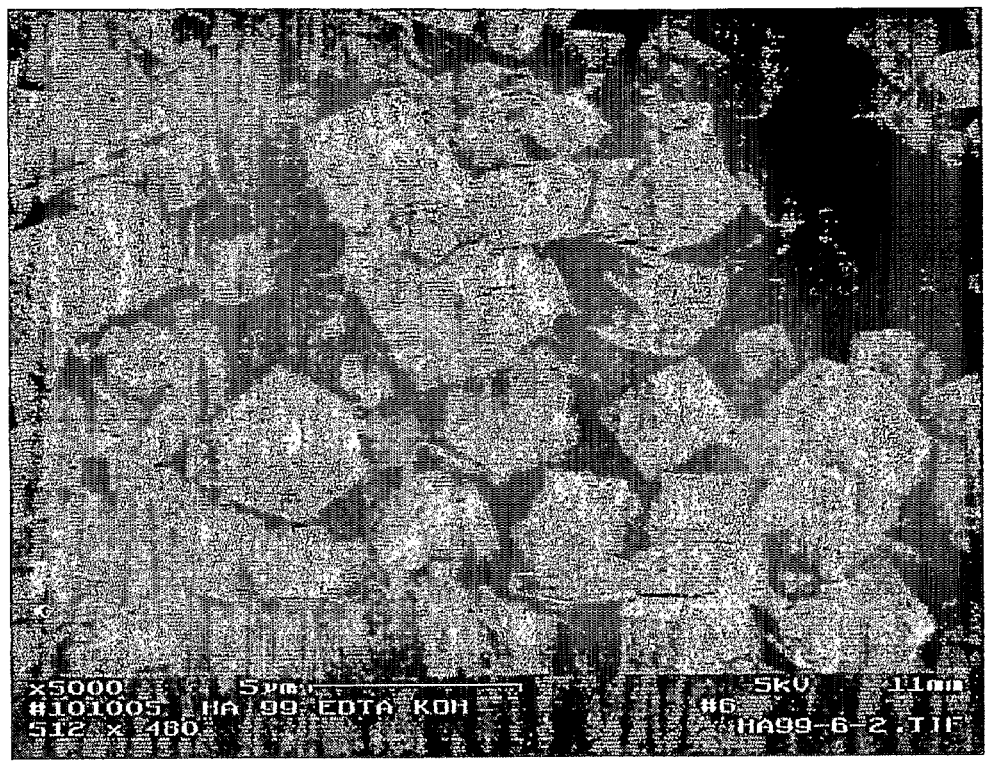
FIG. 8 is a scanning electron microscopy image of hexagonal hydroxyapatite particles having a low aspect ratio.

The term "platelets" is used herein to mean particles in the shape of a hexagon with an aspect ratio less than 1. Exemplary platelets are shown in FIG. 8.

Figure 9:
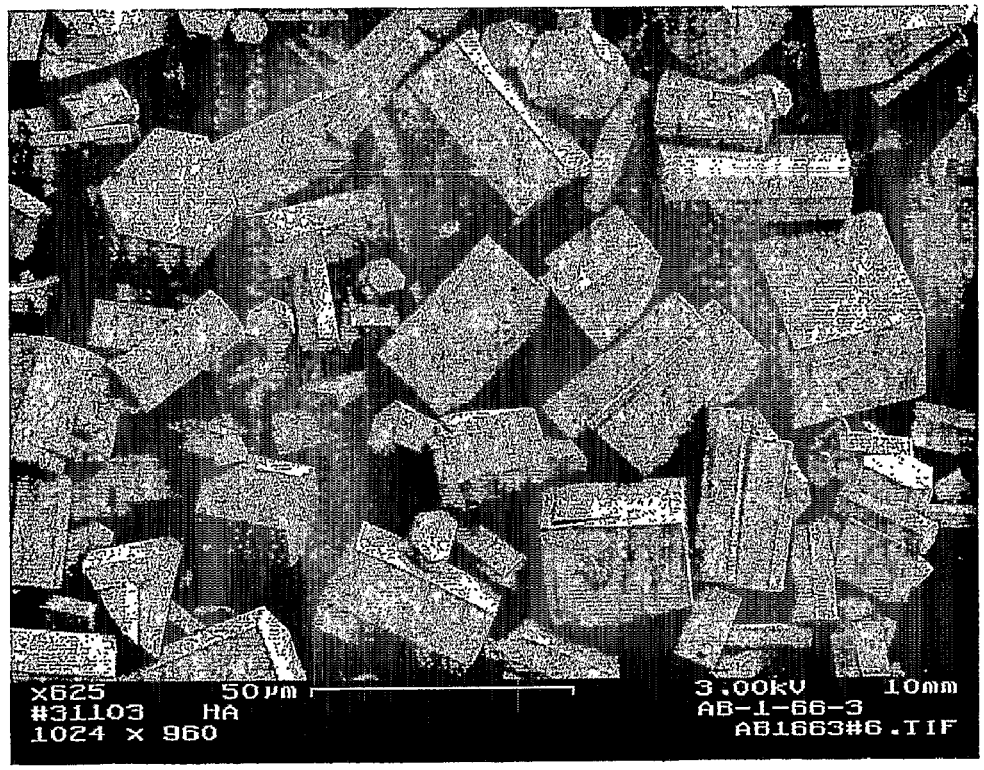
FIG. 9 is a scanning electron microscopy image of hexagonal hydroxyapatite particles having a high aspect ratio.

The term "hexagons" is used herein to mean equiaxed particles in the shape of a hexagon with an aspect ratio of 1-3. Exemplary hexagons are shown in FIGS. 8 and 9.

Figure 12:
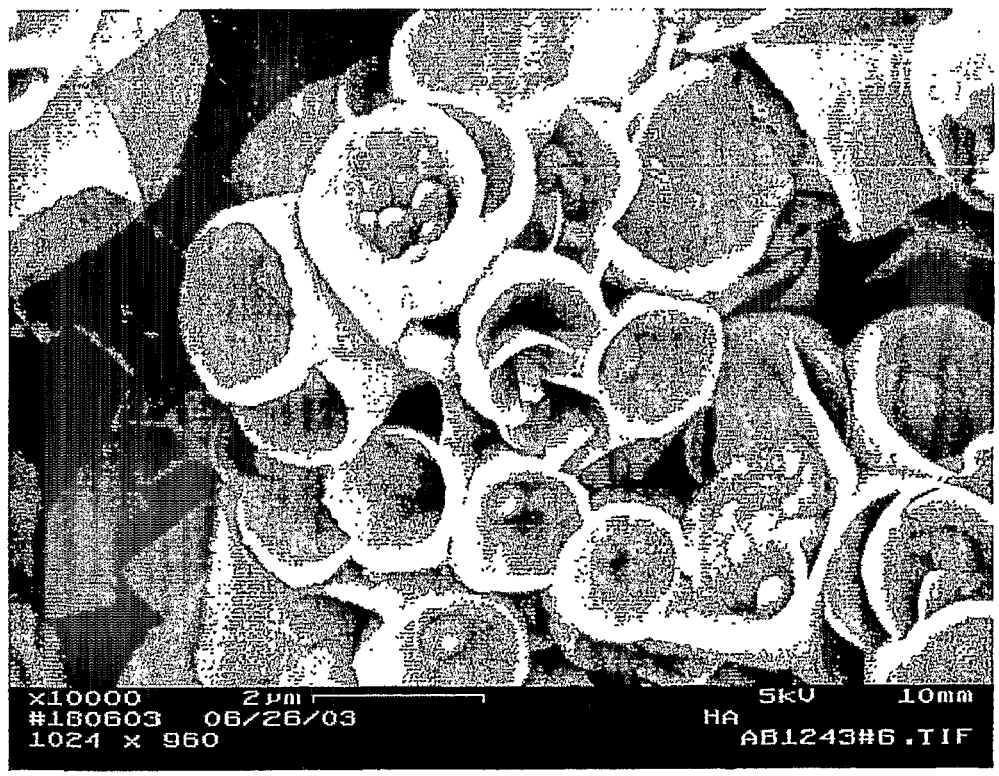
FIG. 12 is a scanning electron microscopy image of tubular hydroxyapatite particles.

The term "tubular" is used herein to mean short tubes with an aspect ratio of about 1, but hollowed out to give the appearance of coral. Exemplary tubular hydroxyapatite is shown in FIG. 12.

Figure 11:
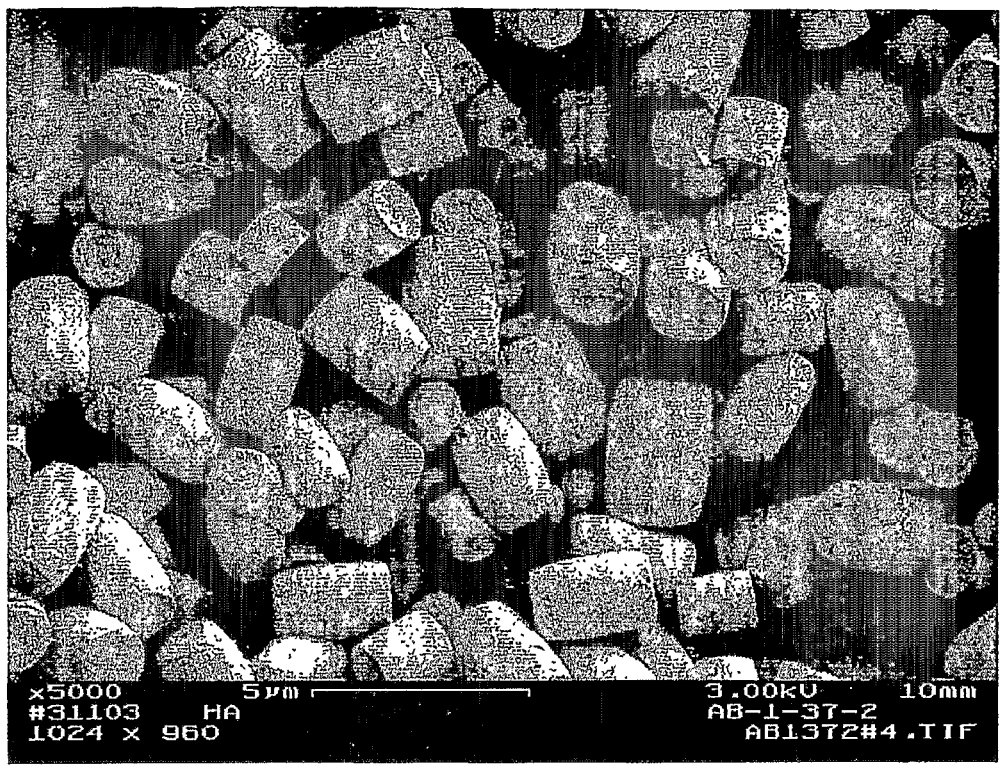
FIG. 11 is a scanning electron microscopy image of barrel hydroxyapatite particles.

The term "barrel" is used herein to mean truncated ellipsoidal particles that appear similar in shape to wooden barrels used to store liquid. Exemplary barrel particles are shown in FIG. 11.

The term "cube-shaped" is used herein to mean any orthogonal single-crystal particles in which the faces are square, rectangular, or both, which possess a cubic morphology. This definition also includes non-perfect cubes, that is, particles with an essentially cubic structure.

Figure 4:
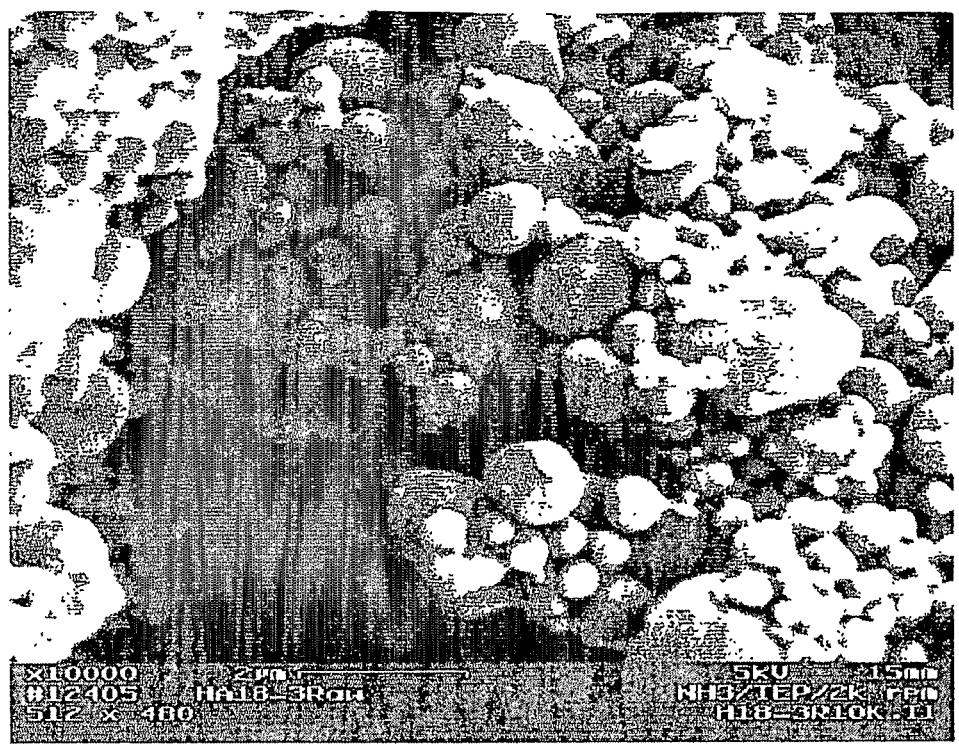
FIG. 4 is a scanning electron microscopy image of smooth spherical hydroxyapatite particles.
Figure 5:
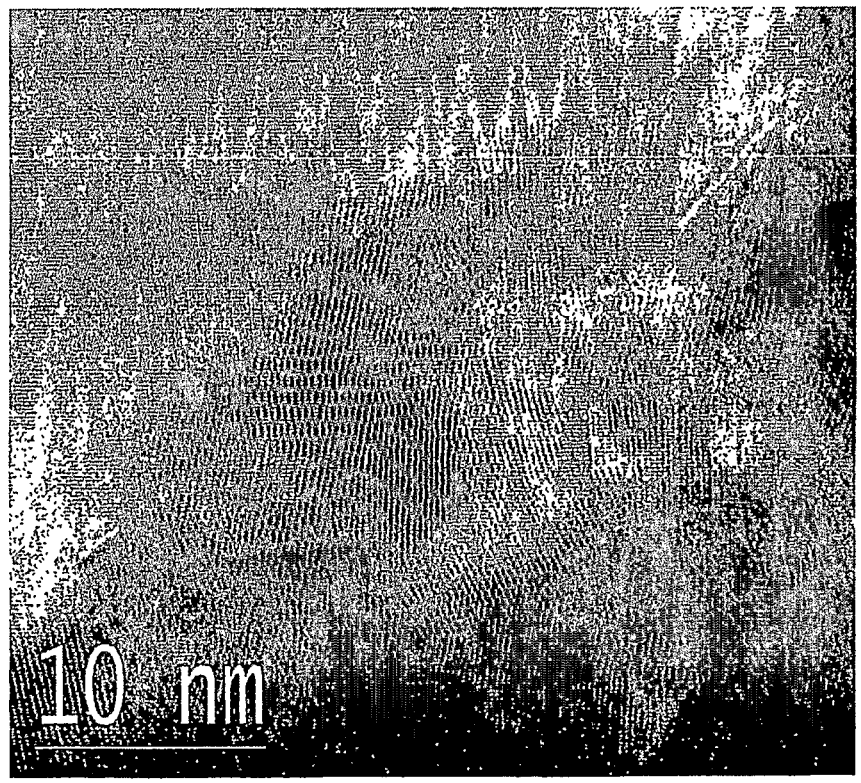
FIG. 5 is a TEM image of the interior surface of the smooth spherical hydroxyapatite particles.

The term "smooth" is used herein to mean a surface that has asperities smaller than the average thickness of the surface. An exemplary smooth particle is shown in FIG. 4.

Figure 6:
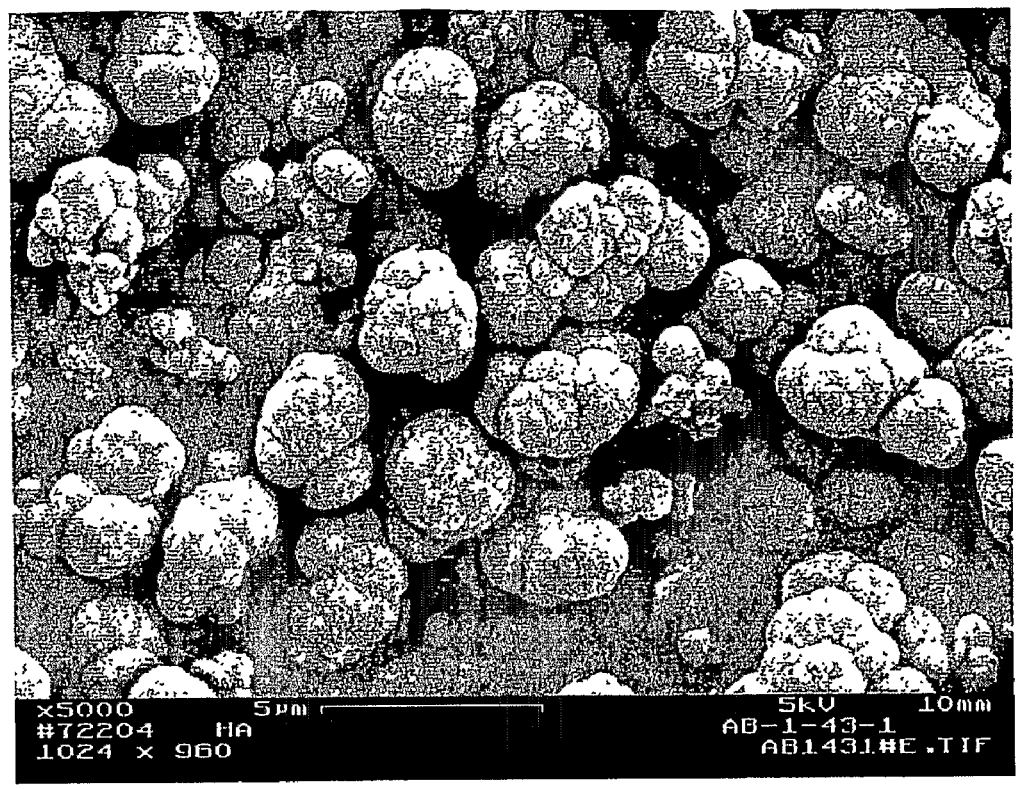
FIG. 6 is a scanning electron microscopy image of rough spherical hydroxyapatite particles.

The term "rough" is used herein to mean a surface that has asperities larger than the average thickness of the surface. An exemplary rough particle is shown in FIG. 6.

The term "passivate" is used herein to mean the formation of a hard and non-reactive dense film on the surface of a substrate that will inhibit corrosion of the substrate.

"Room temperature" is defined herein as 25° C.

"Water-soluble" ion sources are defined as being materials having a solubility in water of at least about 2.0 g/L.

The morphology of the non-agglomerated non-aggregated phase-pure hydroxyapatite of the present invention is controllable. Preferred morphologies include: hexagons with a length that can be controlled from about 50 nm to about 5000 nm and an aspect ratio from about 0.5 to about 5; spheres having hexagonal primary particles and a secondary particle size that can be controlled from about 50 nm to about 5000 nm; tubular particles with a length that can be controlled from about 50 nm to about 5000 nm with an aspect ratio from about 0.5 nm to about 5 nm; and barrel-shaped particles with a length that can be controlled from about 50 nm to about 5000 nm with aspect ratio from about 0.5 to about 5.0.

Preferably, the non-agglomerated non-aggregated phase-pure hydroxyapatite is present in a powder form. The powder may contain one morphology or a mixture of different morphologies.

The characteristics of some exemplary morphologies are set out in FIG. 1.

The hydroxyapatite of the present invention can also be used in a film form, which is made up of grains of hydroxyapatite. The morphology of the grains in the hydroxyapatite film can be controlled. Preferred morphologies for the grains include the same as noted above for the non-agglomerated non-aggregated phase-pure hydroxyapatite.

The hydroxyapatite film can be used to passivate the surface of a substrate, such as, metals, metal oxides, alloys, and polymers stable in alkaline media at elevated temperatures. A preferred metal substrate is titanium. Preferred alloy substrates include mild steel, stainless steel, cobalt/chrome, and titanium alloy. Preferred polymeric substrates include fluoropolymers, polyvinylchloride, and polyethylene terephtalate. Particularly preferred film grain morphology and substrate combinations include a hexagonal grain film on a sapphire single crystal substrate and a cube-shaped grain film on zirconia.

Because the film of the present invention is preferably applied to a substrate by immersing the substrate in a solution and precipitating the film onto the substrate, the film can be coated onto substrates having simple as well as complex shapes with otherwise hard to view interior portions. In this case, reactive sites on the substrate surface define the locations where coatings will occur and the yield of the precipitation reaction will define the thickness of the coating. A reactive site is a surface where the precipitate from the solution can deposit by virtue of a range of bonding mechanisms including, but not limited to, van der Waals, covalent, ionic and metallic mechanisms. Thus, a substrate can be immersed in a liquid and a coating will result of uniform thickness in all locations of the object which have a substrate-liquid interface. Preferred substrate forms include porous substrates, wire meshes, wires, rods, bars, ingots, sheets, and free-form shapes.

The crystalline hydroxyapatite grains may be oriented in a similar direction on the substrate. Additionally, the crystalline hydroxyapatite grains on the substrate surface can have varying lengths.

The texture of the hydroxyapatite film may be manipulated as discussed below to produce a smooth or rough film surface.

Synthetic routes of production of non-agglomerated non-aggregated hydroxyapatite and hydroxapatite films with controllable morphologies are also presented herein. The methods are based on the controlled supply of the ingredients of the precursor to the reaction mixture by using slow degradable components and, optionally, chelating agents. The application of chelating agents makes homogeneous precipitation of hydroxyapatite possible.

In this invention, a solvothermal method is presented that enables hydroxyapatite to be crystallized as a powder or film with controlled crystal size and morphology. In a solvothermal process, single phase or multi-phase reactions using solutions, suspensions, or gels are reacted to crystallize oxides directly from solution typically at temperatures that range from room temperature to about 350° C. and pressures that range from 1 to 500 atm. The solvent medium is typically water where the process is referred to as a hydrothermal process. However, reactions commonly utilize non-aqueous liquids, such as, ethylene glycol, 1,4-butanediol, and ethanol, which can also be co-mixed with water.

Solvothermal synthesis can also use precipitation from homogeneous solution (PFHS) methods for crystallization, giving greater control over morphology and size. In a PFHS reaction, a precipitation reaction is regulated by a chemical reaction that releases a soluble species that is capable of supersaturating a solution and precipitating the thermodynamically and kinetically favored phase. PFHS systems are uniform single-phase solutions that transform to a multi-phase system containing the powder or film of interest. PFHS systems function by controlling the crystallization kinetics, namely the rates of nucleation, growth and even ageing, which are the processes responsible for size and morphology control. For these types of processes, it is important to find the appropriate reactant concentrations, temperatures and pressures where crystallization kinetics are controlled. Compositional, temperature, and pressure uniformity are critical to ensure that all processes occurring the reactor are occurring uniformly. Thus, finding a precipitation process that uses the same chemical components alone is not sufficient to define a suitable PFHS system. PFHS reactions for hydroxyapatite have been developed for both ceramics and films. However, in all of these reactions, attention has been paid to release of the calcium species but not the phosphate species.

In the current invention, the release of phosphorous species is controlled and in some cases, the release of calcium species is also controlled. Phosphoric acid esters of general formula $(RO)_3PO$ were chosen as a source of phosphate ion. In the formula, R is a hydrolyzable water soluble or miscible organophosphate ester leaving group. Examples include hydrogen or an organic hydrocarbon radical hydrolysis derivative of the organophosphate, provided that at least one R is not H. The solubility of tri-organo phosphates decreases with the increase of radical molecular weight. Trimethyl- and triethyl-phosphates are water miscible. Solubility of tripropyl phosphate is 6450 mg/L at 25° C. Solubility of tributyl phosphate is about 1000 mg/L at 4° C. and decreases with temperature, achieving $2.85 \times 10^{-4}$ mg/L at 50° C.

The release of phosphate ion is a multi-step process comprising the set of chemical reactions:

$$(RO)_3PO+H_2O \rightarrow (RO)_2P(OH)O+ROH$$

$$(RO)_2P(OH)O+H_2O \rightarrow ROP(OH)_2O+ROH$$

$$(RO)P(OH)O+H_2O \rightarrow PO_4^{3-}+ROH$$

In alkaline media, substituted phosphoric acids formed in these reactions dissociate according to the equations:

$$(RO)_2P(OH)O \leftrightarrow [(RO)_2P(O)O]^-$$

$$ROP(OH)_2O \leftrightarrow [ROP(OH)O]^- \leftrightarrow [ROP(O)O]^{2-}$$

The optimum balance of solubility and rate of hydrolysis is achieved in tri-ethyl phosphate, although tri-methyl and tri-butyl phosphate can be useful. Derivatives of phosphoric acid esters such as mono- and di-substituted acids also can be used in this process. Other suitable organophosphates include organophosphates in which the organic hydrocarbon groups are alkyl groups with hydrophilic substituents or hydrophilic groups with alkyl components such as alkoxy groups, alkyl carboxylate groups, and the like.

Until now, alkaline hydrolysis of tri-ethyl phosphate (TEP) was limited to hydrolysis of the first ester group with formation of di-ethyl phosphoric acid or its salts. Accordingly, the application of tri-ethyl phosphate in hydroxyapatite synthesis was limited to high temperature processes i.e. above 350 presumably 500° C. At such conditions, however, the uncontrollable degradation of tri-ethyl phosphate occurs.

The present invention employs a hydrothermal tri-ethyl phosphate hydrolysis in which complete hydrolysis of all ester groups is achieved in a relatively slow mode at temperatures below about 300° C., preferably from about 180 to about 250° C., with a controlled release of the phosphate ion. Because of the homogeneous nature of tri-ethyl phosphate hydrolysis in this process, phosphate ion is supplied uniformly over the entire reaction volume with the onset of total hydrolysis of tri-ethyl phosphate, which takes place at about 180° C. Hydrolysis of the first and the second ester groups takes place at lower temperature in agreement with the data of previous researchers.

One of the synthetic routes according to this invention utilizes hydrothermal hydrolysis of TEP in the presence of weak alkali (ammonia). During the first and second steps of hydrolysis, calcium ions, added as a water-soluble salt (nitrate, chloride etc.), partially precipitate at elevated temperature as calcium hydroxide.

The second route of hydroxyapatite synthesis according to the present invention includes using chelating agents, preferably ethylene diamine tetracetic acid (EDTA) and its salts. The function of EDTA in this process is to serve as a chelating agent for calcium, preventing the formation of calcium hydroxide even in the presence of strong alkali (KOH) according to the reaction:

$$Ca^{2+}+EDTA \leftrightarrow [Ca^{2+}EDTA]$$

This shifts the process to homogeneous nucleation, having both the phosphate decomposition and the calcium-EDTA complex decomposition as the rate limiting steps. It is believed that hydrolysis of tri-ethyl phosphate triggers the release of calcium ions from the calcium-EDTA complex with further bonding of the calcium and phosphate moieties into the hydroxyapatite structure.

An exemplary method for producing a phase-pure hydroxyapatite in accordance with the present invention includes dissolving a water-soluble organic or inorganic calcium salt in a solvent; adding a hydrolyzable organophosphate of general formula $(RO)_3PO$ to the solution, wherein R represents an organic hydrocarbon radical, hydrogen, or a hydrolysis derivative of the organophosphate; adding a hydroxide ion source to the solution; and applying heat to the solution.

Also presented is a method for producing a phase-pure hydroxyapatite film, which involves dissolving a chelating agent in a solvent; adding a water-soluble organic or inorganic calcium salt to the solution; adding a hydrolyzable organophosphate of general formula $(RO)_3PO$ to the solution, wherein R represents an organic hydrocarbon radical, hydrogen, or a hydrolysis derivative of the organophosphate; adding a hydroxide ion source to the solution; placing a substrate into the solution; and applying heat to the solution and substrate.

Examples of specific reaction conditions are set out in the Examples section below, and in FIGS. 2 and 3.

Examples of calcium ion sources include calcium hydroxide, calcium carbonate, calcium acetate, calcium halides, calcium oxide, calcium nitrate, calcium phosphate, and the like. Suitable solvents include water and organic solvents.

The optional chelating agent is used for the preparation of films, and also the following HAp particle morphologies: platelets, hexagons, barrels, and tubular structures. Suitable chelating agents include ethylendiamine tetracetic acid and the like.

The solubility of the organophosphate in water is, preferably, not less than 5% by weight at room temperature. Additionally, a preferred organophosphate is one that is miscible with water at room temperature. Examples of suitable organophosphates include tri-ethyl phosphate, tri-methyl phosphate, tri-butyl phosphate, and the like. Derivatives of phosphoric acid esters such as mono- and di-substituted acids also can be used in this process. Organophosphates with hydrophilic alkyl-containing groups can also be used, such as alkoxy groups or alkyl groups with hydrophilic substituents.

Suitable hydroxide ion sources include hydroxide-containing compounds such as ammonium hydroxide, calcium hydroxide, sodium hydroxide, potassium hydroxide, and the like, and compounds that generate hydroxide ion in aqueous solution, such as ammonia, calcium oxide, and the like.

The solution is preferably heated to a temperature less than 300° C. Preferred heating temperatures range from about 180° C. to about 250° C. The solution is preferably reacted in a sealed pressure vessel, such as an autoclave at autogenous pressure up to 500 atm. An autogenous pressure between about 20 and about 25 atm is preferred.

The texture of the HAp films of the present invention can be controlled by adjusting the amount of time the substrate is left in the reactor. For example, the longer the substrate is left in the reactor, the rougher the surface becomes. Surface smoothness or roughness can be verified through visual appearance using SEM. (See FIGS. 4 and 6, for example). In the case of the films of the present invention, steel was observed to provide a smoother film surface than titanium.

In the present invention, texture relates to two aspects: crystallographic orientation and surface shape. In an example of crystallographic orientation, the c-axis of multiple hexgonal rods can be oriented approximately normal to the surface of the substrate. This would create the appearance of the hexagonal rods being vertical. When the rods all have the same approximate length, the rods form a film with just a portion of the rods exposed at the surface of the film. However, when the rods are of varying lengths, the rods protrude at varying lengths from the surface of the film and lead to a varying film topography. These "hills and valleys" of the surface can play a big role in controlling bioactivity. For example, U.S. Pat. No. 6,419,491 a patent recently issued by Ricci that discusses this for dental materials. The disclosure of the Ricci patent is incorporated herein by reference.

There are many reasons why control of the size and morphology of a powder or film would provide utility for devices based on hydroxyapatite. In the biomedical field, materials with controlled morphology means that surfaces have specific crystallographic faces. These faces offer means by which proteins can selectively adsorb. Such an implant would mineralize bone at the interface and thus be osteoconductive. The excellent protein selectivity of this interface would enable the mineralization to proceed faster than a conventional material not having controlled morphology and hence poor protein selectivity. At the same time, it is conceivable that presentation of the appropriate interface in a material can influence biochemistry in a manner where cells in the body can differentiate into bone-producing cells, which could enable bone mineralization in regions where an implant surface is absent. These types of materials are osteoinductive. It has also been reported that the piezoelectric properties are relevant to biomedical applications where bone healing is important.

For applications where piezoelectricity is important, control of the orientation of the crystal relative has a major effect on its electromechanical properties. In many cases, piezoelectric materials are used as mass balances and sensors where adsorption onto its interface can control resonance properties. Thus, the combination of selective adsorption properties and ability to control orientation of the hydroxyapatite crystals could present novel device opportunities for applications such as selective chemical sensing and even frequency control.

In the field of drug delivery, particles or films with well-defined morphology can present numerous advantages. Morphology control offers preferred crystallographic faces that can preferentially adsorb specific drug molecules. By controlling the size of the particles, the solubility and dissolution of the drug can be enhanced as the size of the particles are reduced. In addition, these materials can be synthesized as dispersible colloids. The surface topology or roughness of a film can also be used to enhanced or restrict dissolution. It is also conceivable to incorporate cations and anions to tailor the dissolution properties of hydroxyapatite using ions such as magnesium or carbonate.

For applications such as chromatography, access to crystalline hydroxyapatite with controlled size and morphology can enhance selectivity. Crystals with controlled morphology may selectively adsorb species in a flow stream because the crystallographic faces present specific adsorption sites that are compatible with some molecules and not others. By controlling the size, the probability of access to that surface is increased as the size decreases since there is a concomitant increase in surface area.

Corrosion protection is a novel application for coatings of hydroxyapatite, not previously considered. Such a consideration is reasonable because hydroxyapatite is highly insoluble in aqueous solutions. Furthermore, growth of an adherent insoluble passivating hydroxyapatite layer on a metallic substrate should exhibit excellent performance. The use of sandblasting and other surface roughening techniques allows better film adhesion, giving it limitless metal substrate possibilities.

Given that hydroxyapatite has no toxicity and its components are low cost, such a technology presents great promise for a range of applications including, but not limited to, architectural, automotive, chemical processing, and other applications where corrosion resistance for metallic surfaces is desired. Because hydroxyapatite is insoluble in aqueous solution, these coatings can serve as an effective primer coat. Further, their white color can also provide opportunities for aesthetically white finishes. Varying of synthesis conditions provides an opportunity for dense and porous films as desired. A dense film is defined as a coating where the surface cannot be penetrated far enough to reach the substrate and a porous film is defined as a coating where the substrate is readily and easily accessible to fluid or other mediums.

Devices based on hydroxyapatite are typically in the form of polycrystalline ceramics, polymer-ceramic composites, or films on a metallic surface such as titanium. The powders produced in this invention could be used in conventional processes to make all three forms of materials, using conventional methods such as solid state sintering for polycrystalline ceramics, polymer-melt processing for polymer-ceramic composites and plasma spraying for hydroxyapatite-coated titanium metal. The films in this invention can be used to grow films directly onto the metal surfaces without the need for any high temperature processing. Because hydroxyapatite is insoluble in aqueous solution, these coatings will not dissolve.

The HAp of the present invention is also useful in the preparation of compounds for use as granular fill for direct incorporation into the hard tissues of humans or other animals, and as bone implantable materials. The present invention thus includes granular fill compounds, bone implant materials, tooth filling compounds, bone cements and dentifrices containing the HAp particles and films of the present invention. The products are formulated and prepared by substituting the HAp of the present invention for HAp in conventional HAp-based products. The compounds may be prepared in the form of metallic and polymeric HAp composites.

EXAMPLES

Example 1

Synthesis of Spherical Hydroxyapatite Particles 59 g of calcium nitrate tetrahydrate ($Ca(NO_3)_2 \cdot 4H_2O$ Fisher Scientific) were placed into 482 g of de-ionized water and dissolved under magnetic stirring. After total dissolution of calcium nitrate, 18.3 g of tri-ethyl phosphate (TEP, Aldrich, 99.8+%) were added to the solution and stirred for 10 minutes. Then, 34 g of aqueous ammonia (28%) were added and mixed 5-10 min.

The resulting solution was then filtered through a 0.22 m Millipore filter and loaded into Teflon™ liner. The loaded liner was placed into 1 L autoclave (Model 4531, Parr Instruments) equipped with electrical heater, cooling coil, thermocouple and blade stirrer. Stirring of the reaction mixture was started immediately after the autoclave closing and remained at 1200 rpm during the entire synthesis.

Heat control of the synthesis included heating of the reaction mixture from ambient temperature to 200° C. (1 hour), maintaining temperature of 200±2° C. (24 hours) and cooling to ambient temperature (~20 minutes).

After completion of the synthesis, the reactor was unloaded and product was separated by filtration through a 0.22 m Millipore filter. Hydroxyapatite was washed on the filter 5 times by de-mineralized water and then dried at 85° C. in the laboratory oven.

The prepared HA powder was characterized by powder X-ray diffraction by Kristalloflex D500 diffractometer (Siemens) with Ni-filtered CuKa radiation over the 2 q range 10-80° by a step of 0.02°. Only hydroxyapatite peaks were found. Particle size and morphology were investigated by a field emission scanning microscope (FESEM, Model DSM 962 Gemini, Carl Zeiss-Leo; Philips XL30 FEG-SEM) (FIG. 4) on gold-coated samples. Number mean particles size was determined by light scattering technique (Coulter) as 0.098±0.09 microns.

Example 2

Control of Spherical Hydroxyapatite Particle Size 59 g of calcium nitrate tetrahydrate ($Ca(NO_3)_2*4H_2O$ Fisher Scientific) were placed into 482 g of de-ionized water and dissolved under magnetic stirring. After total dissolution of calcium nitrate, 18.3 g of tri-ethyl phosphate (TEP, Aldrich, 99.8+%) were added to the solution and stirred for 10 minutes. Then, 34 g of aqueous ammonia (28%) were added and mixed 5-10 min.

The solution was then filtered through a 0.22 m Millipore filter and loaded into a Teflon™ liner. The loaded liner was placed into a 1 L autoclave (Model 4531, Parr Instruments) equipped with an electrical heater, cooling coil, thermocouple, and blade stirrer. Stirring of the reaction mixture was started immediately after the autoclave closing and sustained during the entire synthesis at the chosen rotation speed. In consequent syntheses with the identical recipe 200, 700 and 1700 rpm were maintained through the entire synthesis.

Heat control of the synthesis included heating the reaction mixture from ambient temperature to 200° C. (1 hour), maintaining temperature of 200±2° C. (24 hours) and cooling to ambient temperature (~20 minutes).

After completion of the synthesis, the reactor was unloaded and the product was separated by filtration through a 0.22 m Millipore filter. Hydroxyapatite was washed on the filter 5 times by de-mineralized water and then dried at 85° C. in the laboratory oven.

Figure 7:
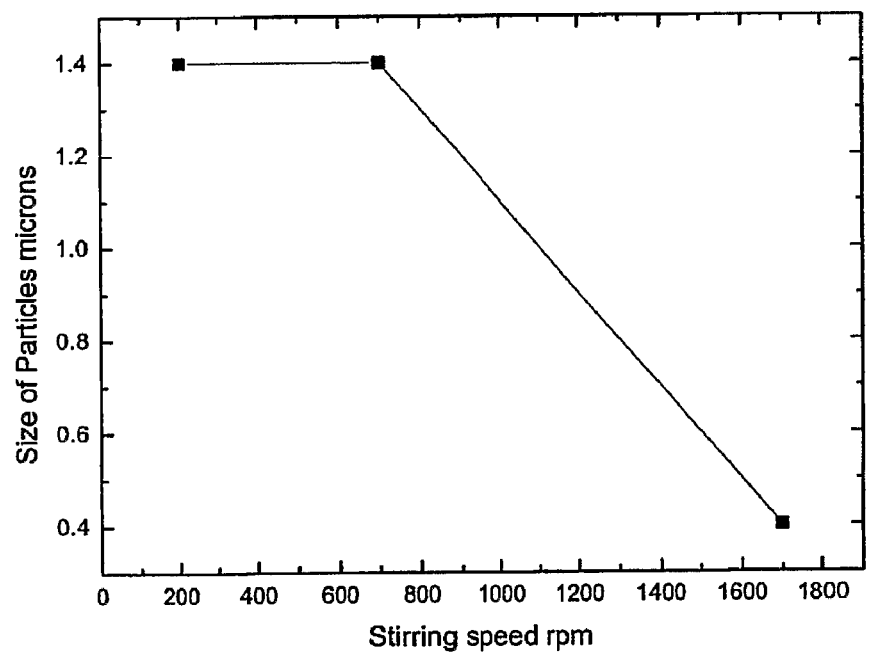
FIG. 7 is a graph showing spherical particle size as a function of stirring speed.

The prepared HAp powder was characterized by powder X-ray diffraction by Kristalloflex D500 diffractometer (Siemens) with Ni-filtered CuKa radiation over the 2 q range 10-80° by a step of 0.02°. Only hydroxyapatite peaks were found. Particle size and morphology were investigated by a field emission scanning microscope (FESEM, Model DSM 962 Gemini, Carl Zeiss-Leo; Philips XL30 FEG-SEM) on gold-coated samples. Spherical hydroxyapatite morphologies are shown in FIGS. 4 and 6. Dependence of size of the particles vs rotation speed is presented in FIG. 7.

Example 3

Synthesis of Hexagonal Hydroxyapatite Particles 0.44 g of EDTA (Fisher Scientific) were dissolved in 58.3 g of de-mineralized water. Then, 0.35 g of calcium nitrate tetrahydrate ($Ca(NO_3)_2*4H_2O$ Fisher Scientific) were placed into solution and dissolved under magnetic stirring. After total dissolution of calcium nitrate, 0.22 g of tri-ethyl phosphate (TEP, Aldrich, 99.8+%) were added to the solution and stirred for 10 minutes. Then, 0.67 g of potassium hydroxide were added and mixed until total dissolution.

The solution was then filtered through a 0.22 m Millipore filter and loaded into a Teflon™ liner. The loaded liner was placed into a 125 ml autoclave (Model 4748, Parr Instruments). The reactor was placed in a preheated to 180° C. laboratory oven (Fisher Scientific Isotemp oven, model 655G) for 20 hours. Due to high thermal inertia of the massive autoclave, working temperature was achieved in about 4 hours.

After completion of the synthesis, the reactor was cooled by quenching in running cold tap water for 30 minutes, unloaded, and product was separated by filtration through a 0.22 m Millipore filter. Hydroxyapatite was washed on the filter 5 times by de-mineralized water and then dried at 85° C. in the laboratory oven.

The prepared HA powder was characterized by powder X-ray diffraction by Kristalloflex D500 diffractometer (Siemens) with Ni-filtered CuKa radiation over the 2 q range 10-80° by a step of 0.02°. Only hydroxyapatite peaks were found. Particle size and morphology were investigated by a field emission scanning microscope (FESEM, Model DSM 962 Gemini, Carl Zeiss-Leo; Philips XL30 FEG-SEM) on gold-coated samples.

For the preparation of low aspect ratio hexagons, 2.63 g EDTA, 2.13 g $Ca(NO_3)_2$, 1.32 g TEP, and 4.03 g KOH were dissolved in 49.89 ml of de-mineralized water. The oven was preheated to 200° C. and total duration of synthesis was 25 hours. Cooling of the reactor, washing, separation and characterization of hydroxyapatite followed the procedure described above. Morphology of the obtained in this synthesis hydroxyapatite is illustrated by microphotograph in FIG. 8.

Example 4

Control of Hexagonal Hydroxyapatite Particle Size

Figure 10A:
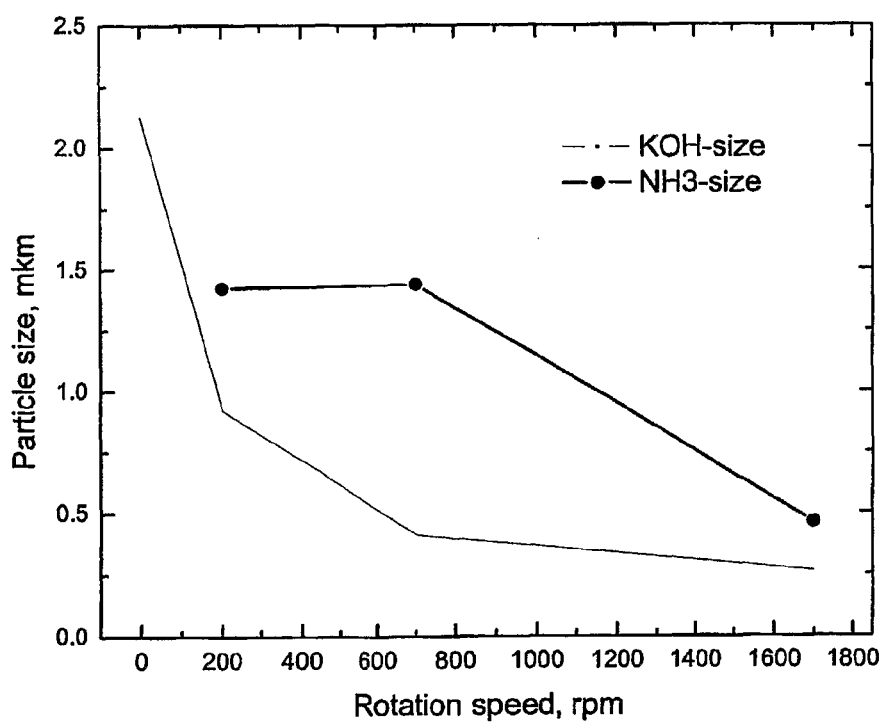
FIG. 10*a* is a graph showing the effect of rotation speed on particle size.

Control over the aspect ratio and size of hexagonal hydroxyapatite particles was achieved by variation of reagent concentration, temperature, and time of synthesis. Amounts of EDTA, ($Ca(NO_3)_2*4H_2O$), TEP, and KOH are presented in FIG. 10.

EDTA (Fisher Scientific) was dissolved in de-mineralized water. Then, calcium nitrate tetrahydrate ($Ca(NO_3)_2*4H_2O$ Fisher Scientific) were placed into solution and dissolved under magnetic stirring. After total dissolution of calcium nitrate, tri-ethyl phosphate (TEP, Aldrich, 99.8+%) was added to the solution and stirred for 10 minutes. Then, potassium hydroxide was added and mixed until total dissolution.

The solution was then filtered through a 0.22 m Millipore filter and loaded into a Teflon™ liner. The loaded liner was placed into a 125 ml autoclave (Model 4748, Parr Instruments). The reactor was placed into a laboratory oven preheated to working temperature specified in FIG. 10 (Fisher Scientific Isotemp oven, model 655G) for 20 or 40 hours.

After completion of the synthesis, the reactor was cooled by quenching in running cold tap water for 30 minutes, unloaded, and product was separated by filtration through a 0.22 m Millipore filter. Hydroxyapatite was washed on the filter 5 times by de-mineralized water and then dried at 85° C. in the laboratory oven.

The prepared HAp powder was characterized by powder X-ray diffraction by Kristalloflex D500 diffractometer (Siemens) with Ni-filtered CuKa radiation over the 2 q range 10-80° by a step of 0.02°. Only hydroxyapatite peaks were found. Particle size and morphology were investigated by a field emission scanning microscope (FESEM, Model DSM 962 Gemini, Carl Zeiss-Leo; Philips XL30 FEG-SEM) on gold-coated samples.

Aspect ratio and length of the particles were measured directly in the images using Adobe Photoshop 5.5.

Example 5

Synthesis of Barrel-Type Hydroxyapatite Particles 0.44 g of EDTA (Fisher Scientific) were dissolved in 58.3 g of de-mineralized water. Then, 0.35 g of calcium nitrate tetrahydrate (Ca(NO$_3$)$_2$*4H$_2$O Fisher Scientific) were placed into solution and dissolved under magnetic stirring. After total dissolution of calcium nitrate 0.22 g of tri-ethyl phosphate (TEP, Aldrich, 99.8+%) were added to the solution and stirred for 10 minutes. Then, 0.67 g of potassium hydroxide were added and mixed to total dissolution.

The solution was then filtered through a 0.22 m Millipore filter and loaded into a Teflon™ liner. The loaded liner was placed into a 125 ml autoclave (Model 4748, Parr Instruments). The reactor was mounted on a magnetic stirrer and heated with electrical tape to working temperature of 230° C. during 1 hour. Total duration of the synthesis is 24 hours.

After completion of the synthesis, the reactor was cooled at the room temperature of about 25° C. during 2 hours, unloaded and product was separated by filtration through a 0.22 m Millipore filter. Hydroxyapatite was washed on the filter 5 times by de-mineralized water and then dried at 85° C. in the laboratory oven.

The prepared HA powder was characterized by powder X-ray diffraction by Kristalloflex D500 diffractometer (Siemens) with Ni-filtered CuKa radiation over the 2 q range 10-80° by a step of 0.02°. Only hydroxyapatite peaks were found. Particle size and morphology were investigated by a field emission scanning microscope (FESEM, Model DSM 962 Gemini, Carl Zeiss-Leo; Philips XL30 FEG-SEM) on gold-coated samples. Morphology of the obtained in this synthesis hydroxyapatite is illustrated by microphotograph in FIG. 11.

Example 6

Synthesis of Hydroxyapatite Film 0.44 g of EDTA (Fisher Scientific) were dissolved in 58.3 g of de-mineralized water. Then, 0.35 g of calcium nitrate tetrahydrate (Ca(NO$_3$)$_2$*4H$_2$O Fisher Scientific) were placed into solution and dissolved under magnetic stirring. After total dissolution of calcium nitrate 0.22 g of tri-ethyl phosphate (TEP, Aldrich, 99.8+%) were added to the solution and stirred for 10 minutes. Then 0.67 g of potassium hydroxide were added and mixed till total disolution.

Solution was filtered through a 0.22 m Millipore filter and then loaded into a Teflon™ liner. The loaded liner was placed into a 125 ml autoclave (Model 4748, Parr Instruments). Sample of the mild steel 1008 was roughened with sand paper #320 and then placed into autoclave in inclined position under the angle about 60°. Reactor was placed in a preheated 195° C. laboratory oven (Fisher Scientific Isotemp oven, model 655G) for 15.3 hours.

Following completion of the reaction, the reactor was air cooled at room temperature about 25° C. during 2 hours. The coated sample was washed 5 times by de-mineralized water and then air dried at room temperature.

Figure 13:
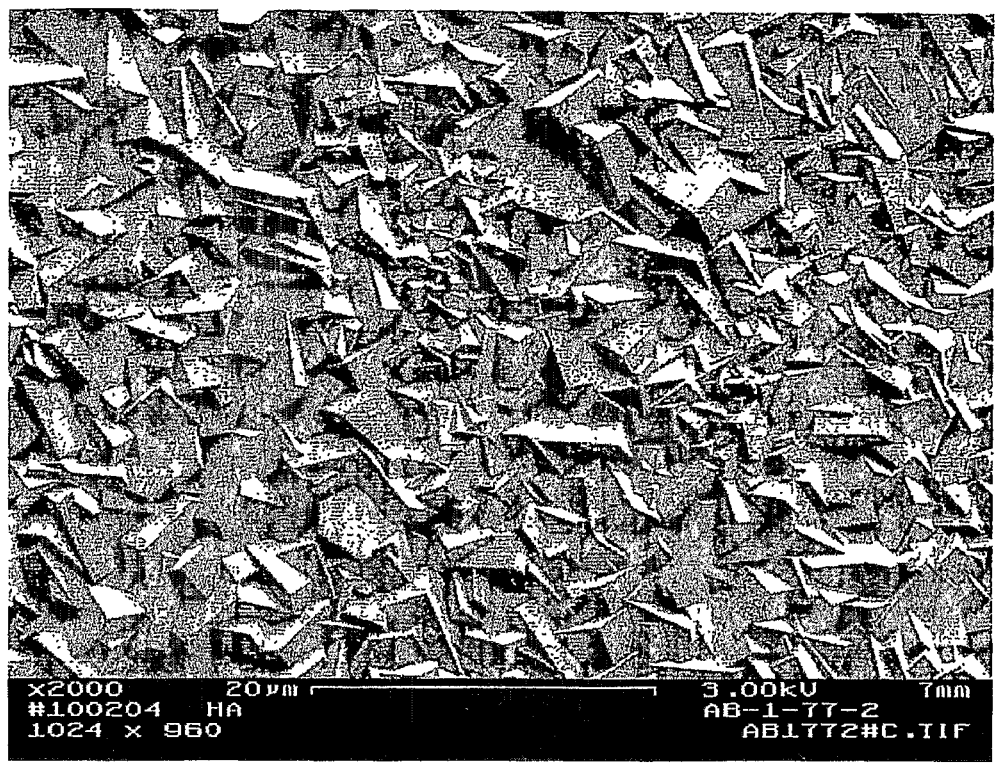
FIG. 13 is a scanning electron microscopy image of a hydroxyapatite coating on mild steel.
Figure 14:
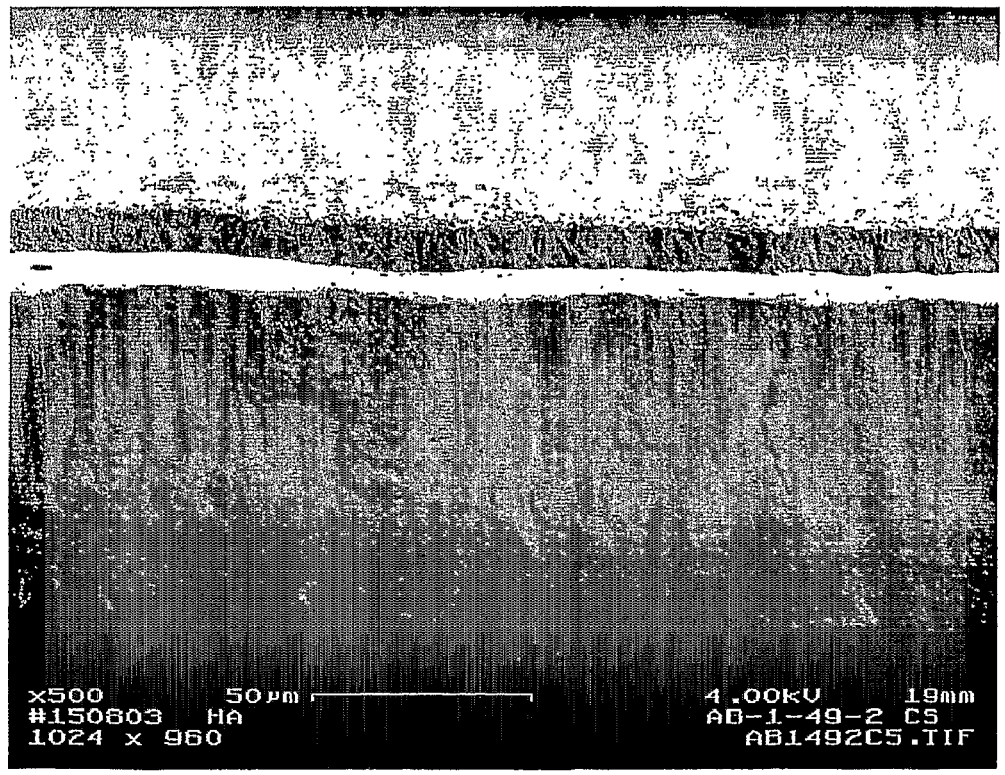
FIG. 14 is a scanning electron microscopy image of a hydroxyapatite coating on stainless steel.
Figure 15:
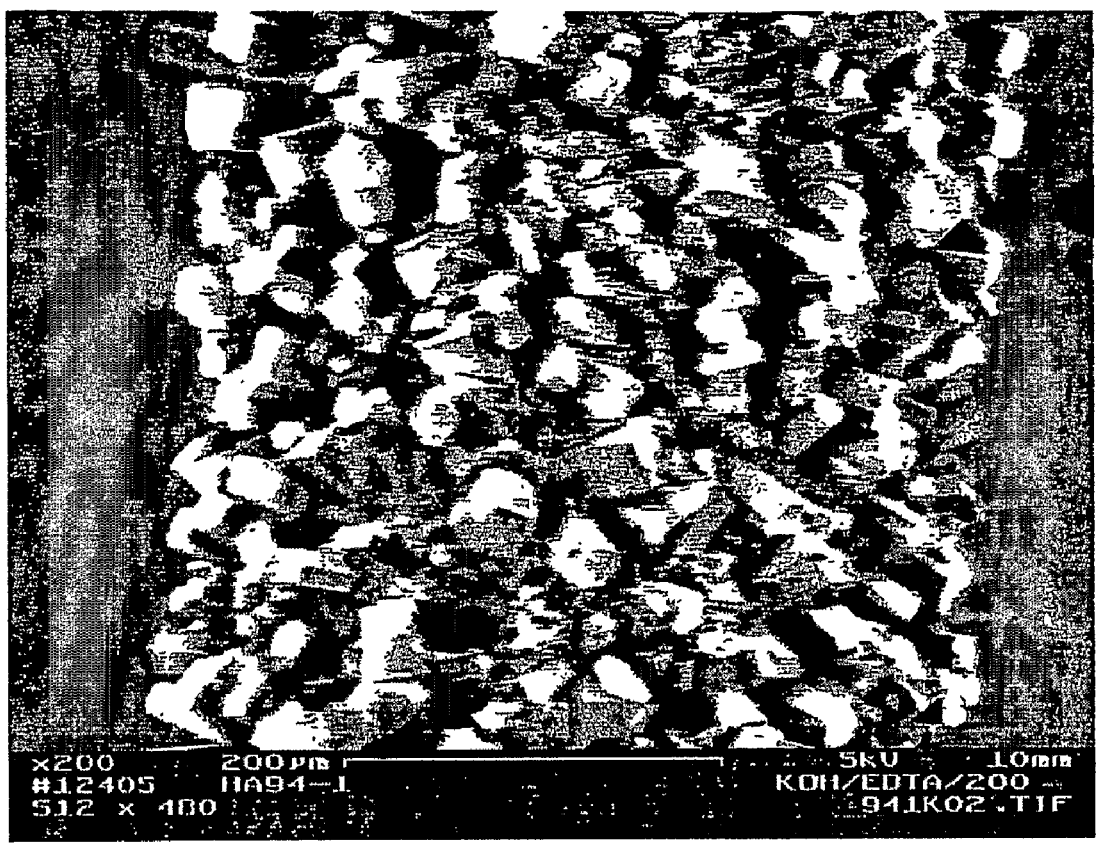
FIG. 15 is a scanning electron microscopy image of a hydroxyapatite coating on titanium wire.
Figure 16A:
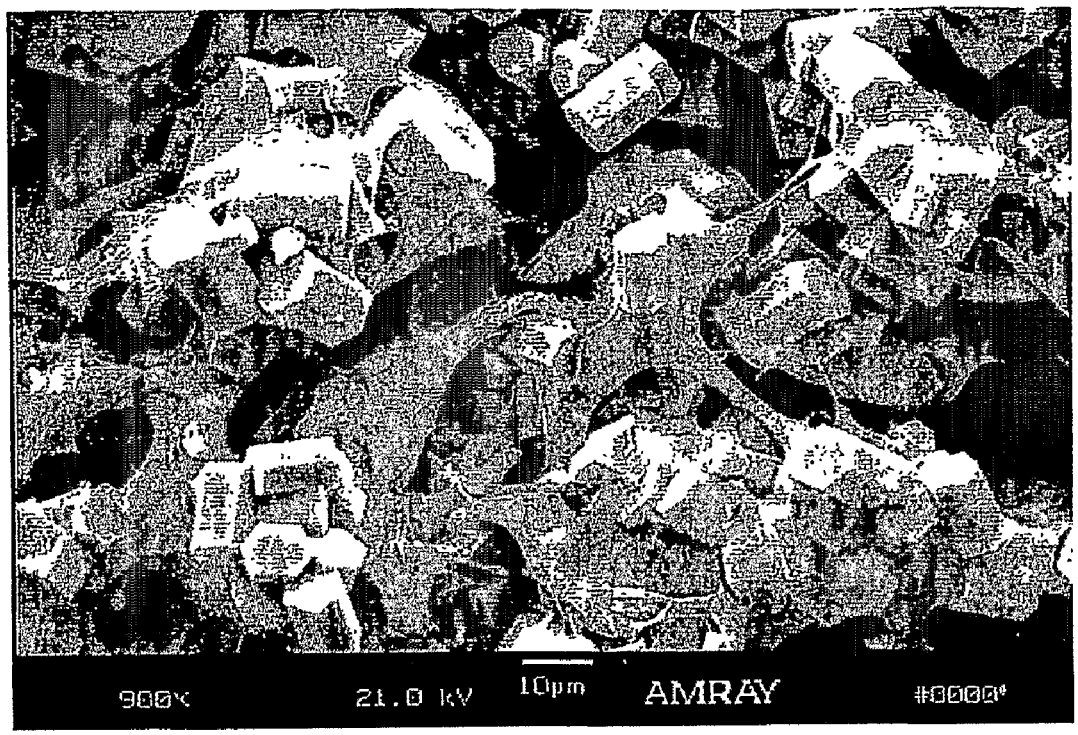
FIGS. 16*a-d* are scanning electron microscopy images of cell spreading on hexagonal hydroxyapatite.
Figure 16B:
Figure 16C:
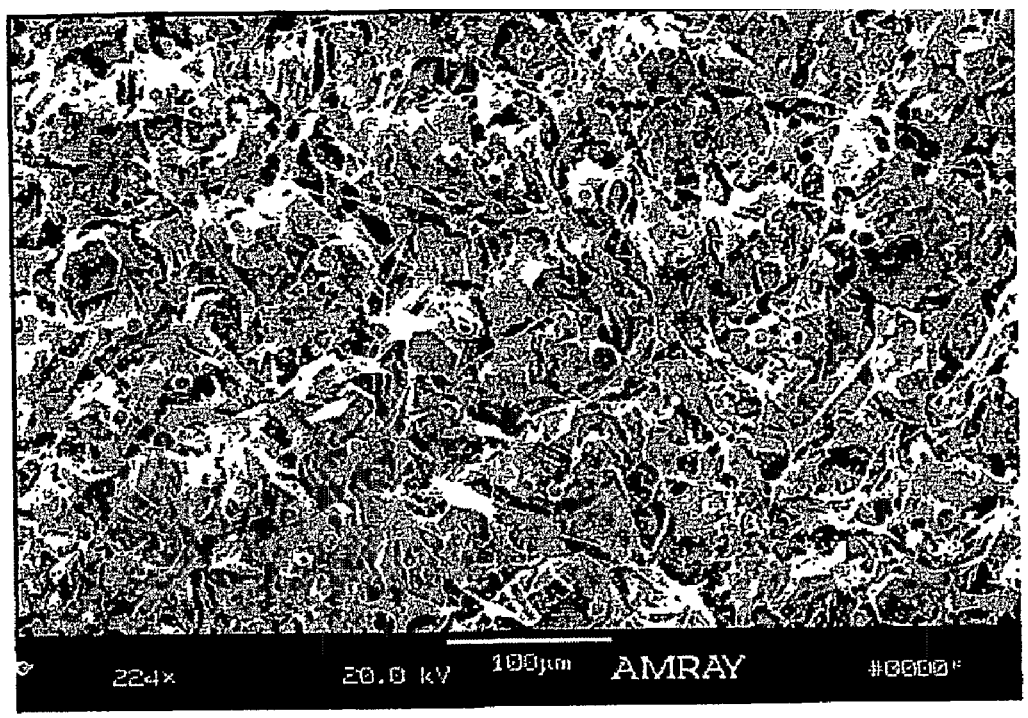
Figure 16D:
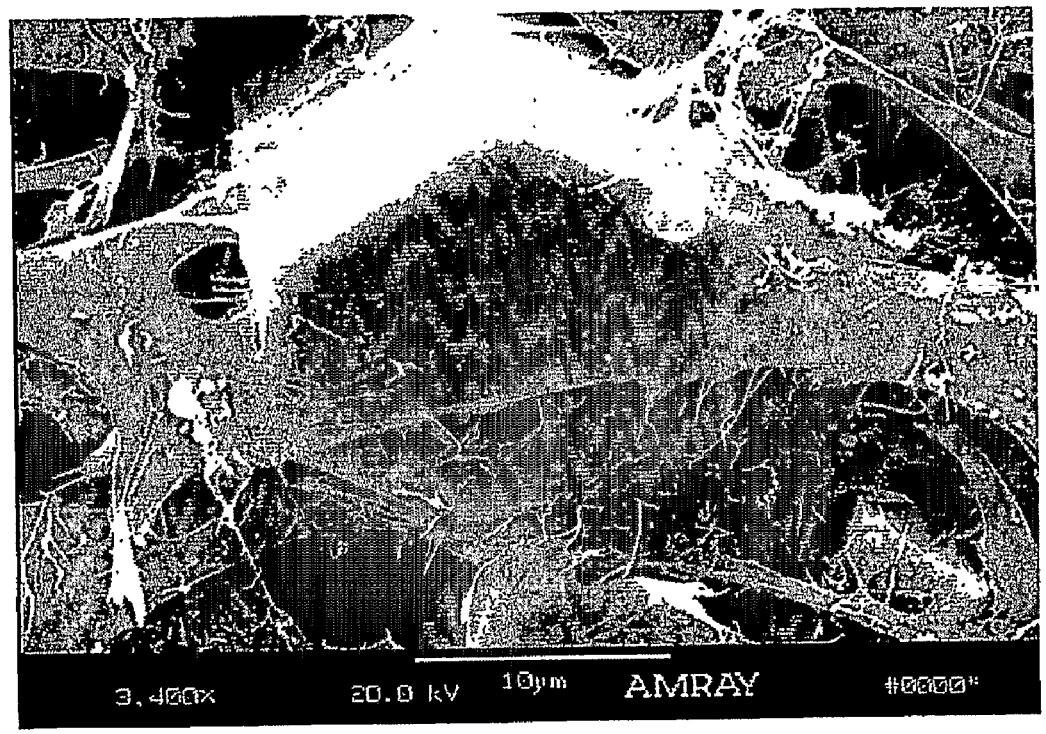

The coating was investigated by a field emission scanning microscope (FESEM, Model DSM 962 Gemini, Carl Zeiss-Leo; Philips XL30 FEG-SEM) on gold-coated samples. Images of hydroxyapatite coatings are found in FIGS. 13-15.

Coatings were additionally deposited on grit blasted substrates at 14 and 26 hours to evaluate the film deposition process. FIGS. 21*a-b* and 22*a-b* illustrate the results of XRD analysis of these samples. All 2Theta XRD scans demonstrate that the HA 002 peak, at approximately 25.80, whose intensity in a random sample is 33-40% (PDF 60-9633, 09-0432) of the HA 211 100% peak at 31.70, has a higher absolute intensity than the 211 peak. This suggests that there are more 002 planes diffracting, more c-axis's orthogonal to the substrate surface, than observed in a randomly oriented/textured sample.

002 pole figures for these samples quantify this observation. Nearly all 002 planes are distributed from 0-600 from the substrate's orthogonal in a roughly gaussian manner, with increasing intensity (002 plane population) as the lower psi angles are approached. Further inspection of pole figure data indicates that an increase in the magnitude of or a refinement of the texturing may occur with increasing with synthesis time. From 14 hours to 26 hours, the peak intensity increases steadily from 10,322 a.u. at 50 psi to 13,133 a.u. at 1.00 psi.

Example 7

Biocompatibility of Hydroxyapatite Films

To test the basic biocompatibility of the hydroxyapatite coating, osteoblast adhesion (spreading) was observed by SEM and osteoblast proliferation was quantitatively measured with the CyQuant DNA binding dye. Cell spreading is a qualitative means used to measure the cellular biocompatibility of a surface because cells tend to maximize their surface area in contact with desirable/biocompatible surfaces by spreading out and tend to minimize their surface area in contact with non-biocompatible surfaces by becoming spherical. Cell proliferation is measured to evaluate the surface's ability to maintain a cell population.

Two hydroxyapatite coated samples synthesized for 18.5 hours were used for testing cell adhesion. MC3T3-E1 pre-osteoblast cells were seeded onto the coatings as well as onto tissue culture plastic that served as controls. Cells were incubated at 370 and 5% CO$_2$ in cell media (a-MEM, 10% FBS+ P/S/glu). After 93 hours and 190.25 hours, samples were fixed and prepared for examination by SEM. Three hydroxyapatite coated samples synthesized for 20.5, 18, and 18 hours were used for CyQuant cell proliferation testing. MC3T3-E1 pre-osteoblast cells were seeded onto the samples and onto tissue culture plastic controls. The CyQuant assay was carried out as per kit instructions.

FIGS. 16*a-d* are representative micrographs of the osteoblast cells on the coating at 93 hours and 190.25 hours. It can be observed that the cells are extensively spread out on the coating surface. In fact, many cells are observed to have increased their cell surface area in contact with the coating to such an extensive degree that the sharp contours of the underlying crystals are seen through the cells. Cell processes can also been seen spanning the troughs between crystals. By comparing the micrographs from 93 hours and 190.25 hours, cell proliferation on the coating can easily be observed qualitatively.

Figure 17:
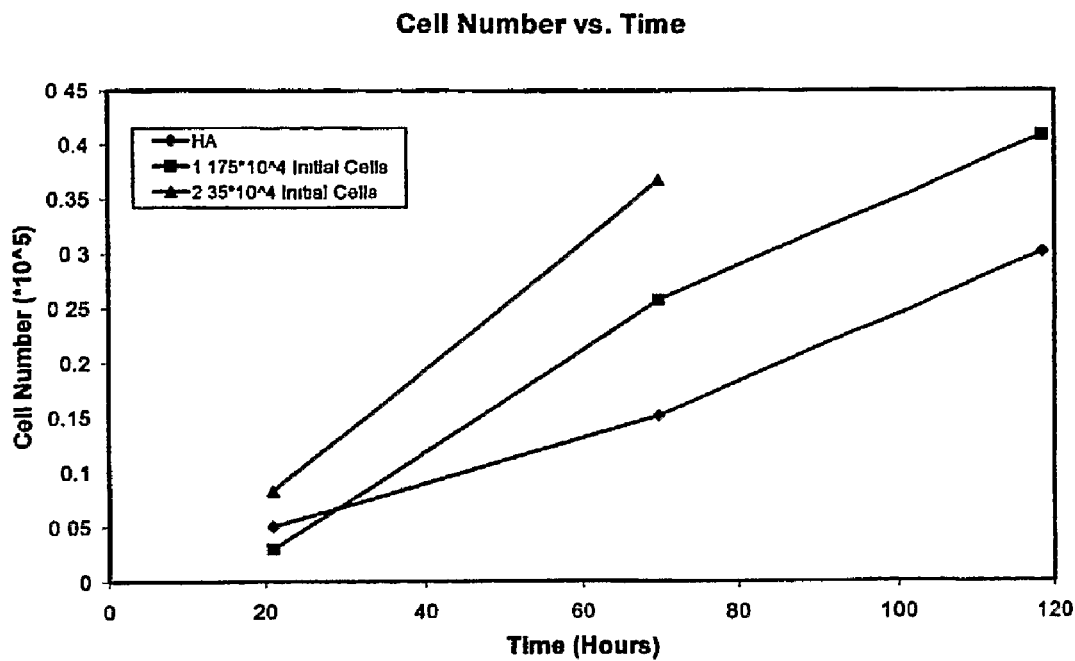
FIG. 17 is a graph showing cell proliferation with CyQuant DNA content as a function of time.

FIG. 17 illustrates the results of the cell proliferation assay. Over the first 70 hours (3 days) osteoblasts proliferate on the HA coating, but at a slower rate than that seen on tissue culture plastic controls. Between 3 and 5 days, however, the proliferation rate is roughly equal on both substrates. It is observed that the cell numbers calculated at 20 hours are systematically less than the seeded density, which is assumed to be due to an error in the dilution series used to make the standard curve. The standard curve for this assay is a straight line, thus, only the absolute cell number is incorrect. As a measure of biocompatibility the results above indicate that the HA coating is indeed biocompatible—osteoblasts actively maximize their surface area in contact with the coating and the coating supports cell proliferation.

Osteoblast Cell Activity

Figure 18:
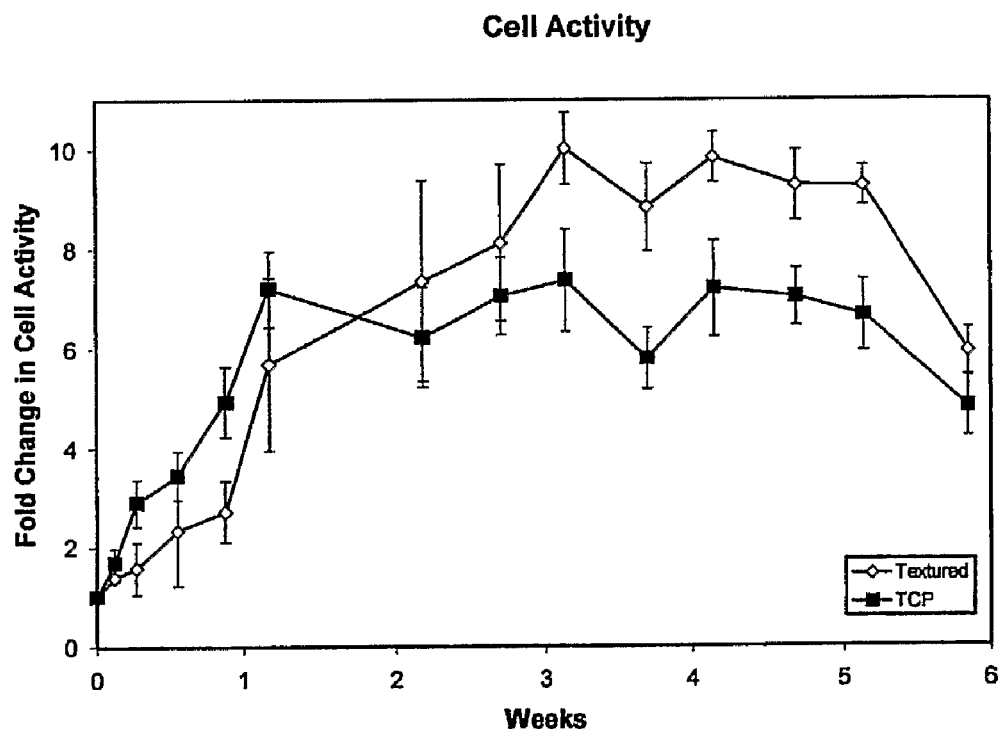
FIG. 18 is a graph comparing cell metabolic activity for hydroxyapatite versus TCP.

Alamar blue, a dye that is reduced by the metabolic intermediates NADPH/NADP, FADH/FAD, FMNH/FMN, and NADH/NAD was used to measure total metabolic activity of cells seeded onto textured HA coatings, randomly oriented HA coatings, and tissue culture plastic (TCP). FIG. 18 demonstrates that cell activity increases slightly slower on textured HA coating than TCP over the first week in culture, on average. However, after week one, activity is higher on textured coatings, and significantly higher from 3-5 weeks in culture. Furthermore, peak activity on HA is almost 36% greater than peak intensity on TCP.

Figure 19:
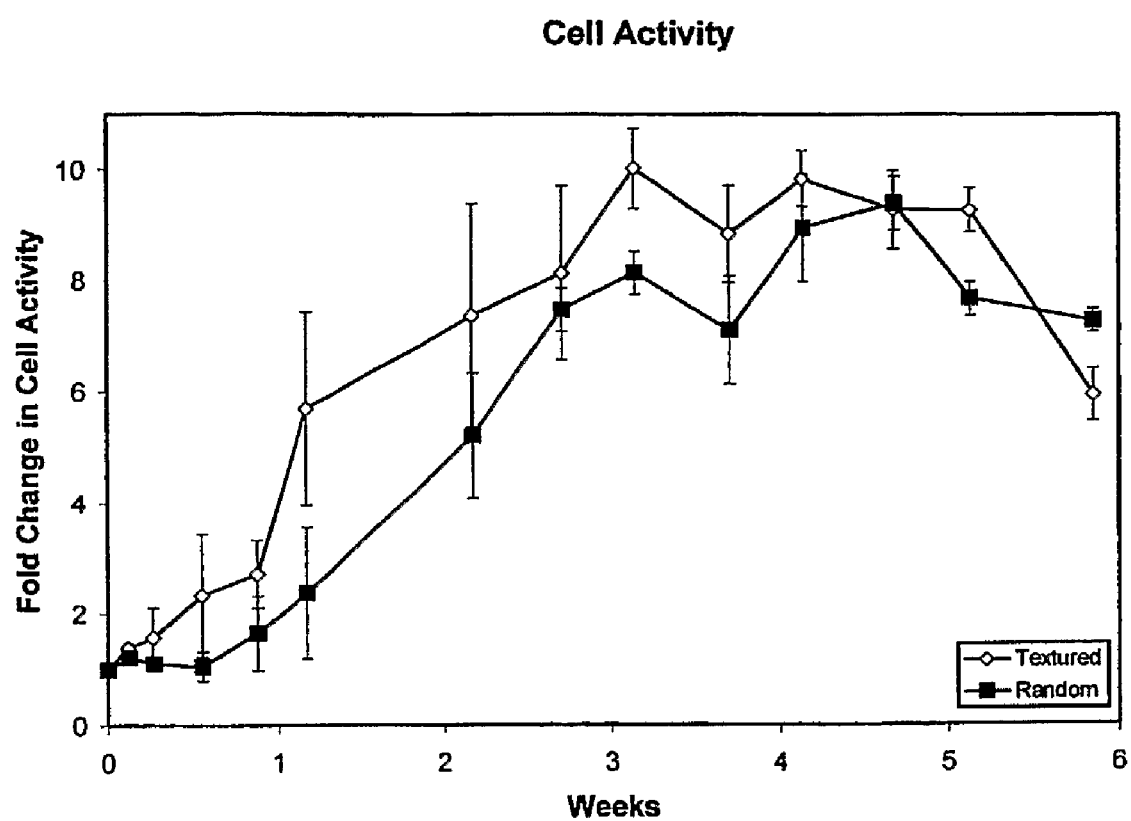
FIG. 19 is a graph comparing the effect of texture on cell metabolic activity.
Figure 20A:
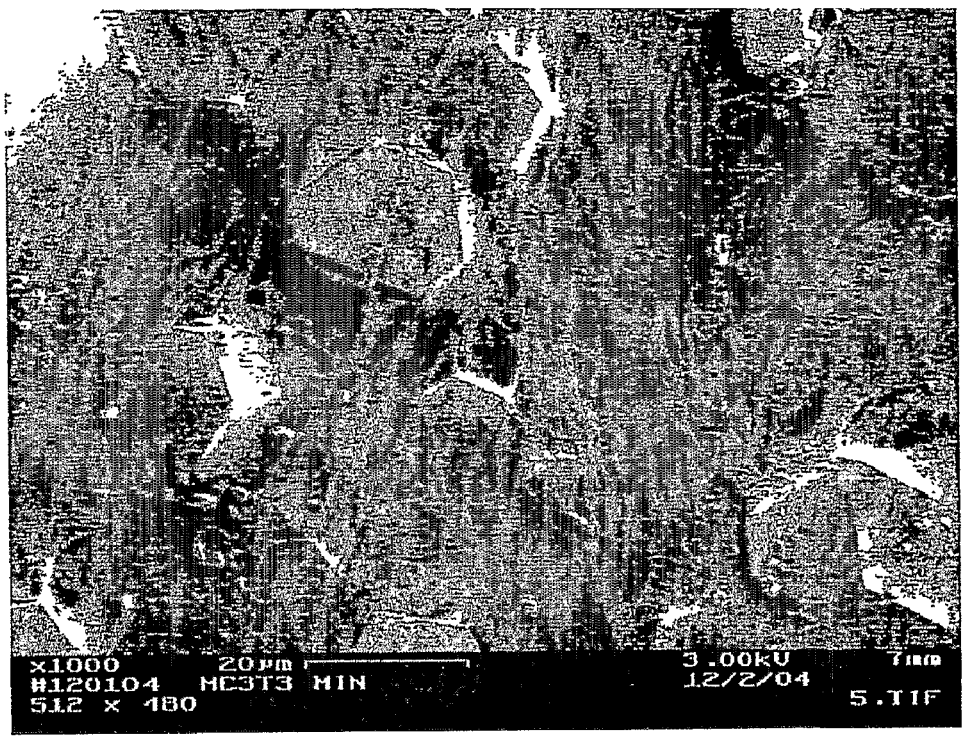
FIGS. 20*a-d* are scanning electron microscopy images of osteoblast mineralization on hydroxyapatite.
Figure 20B:
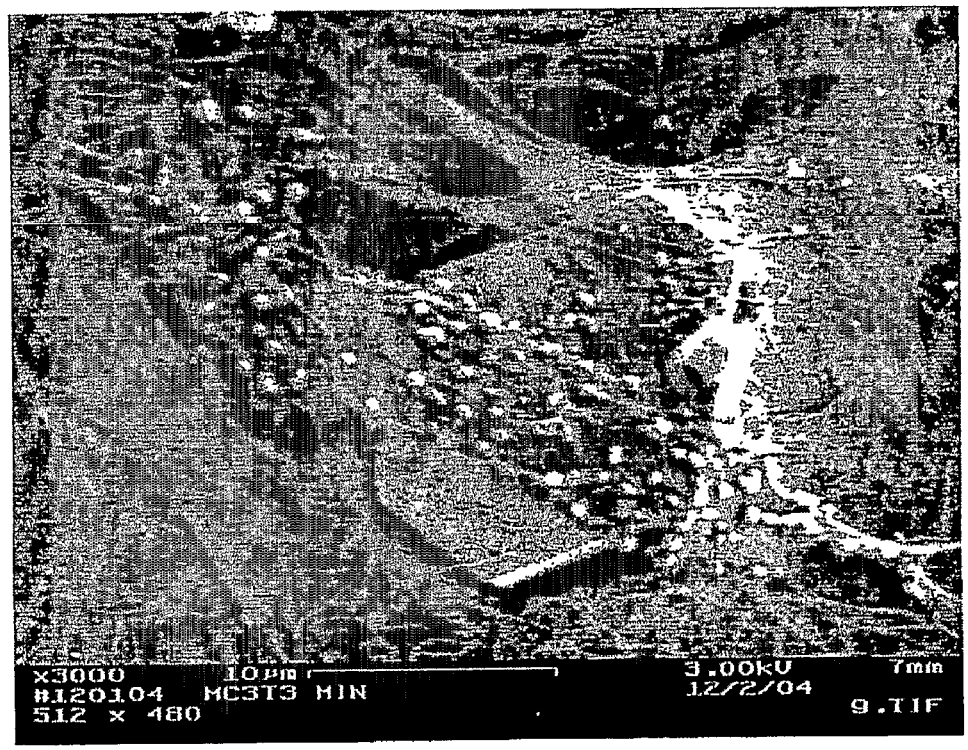
Figure 20C:
Figure 20D:
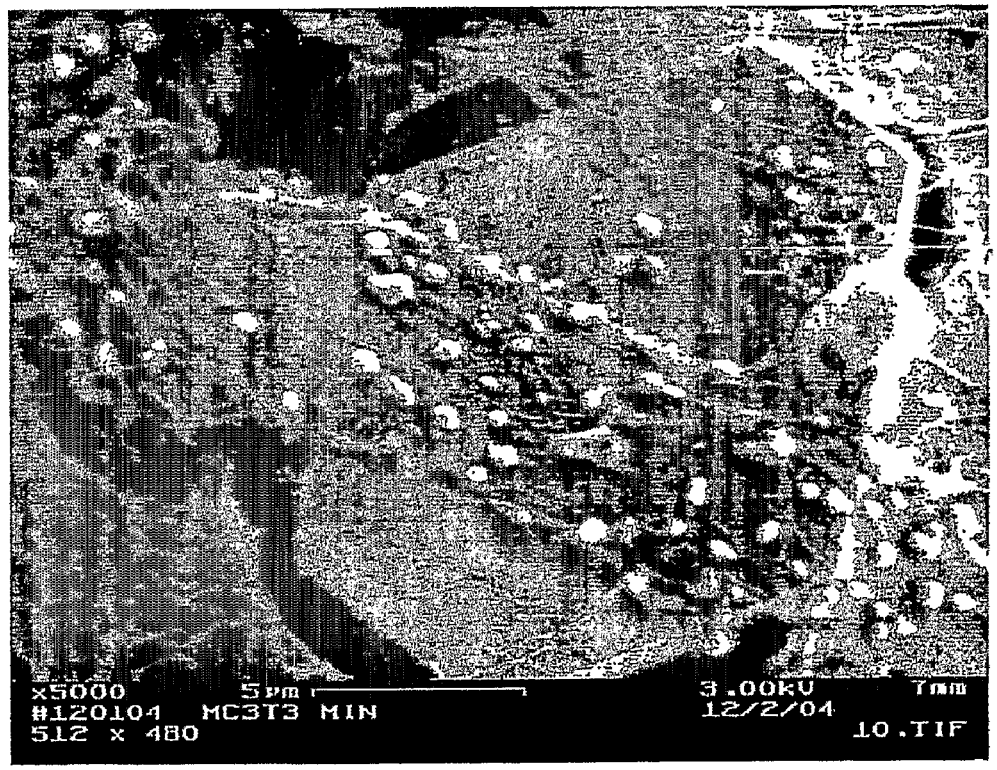
Figure 21A:
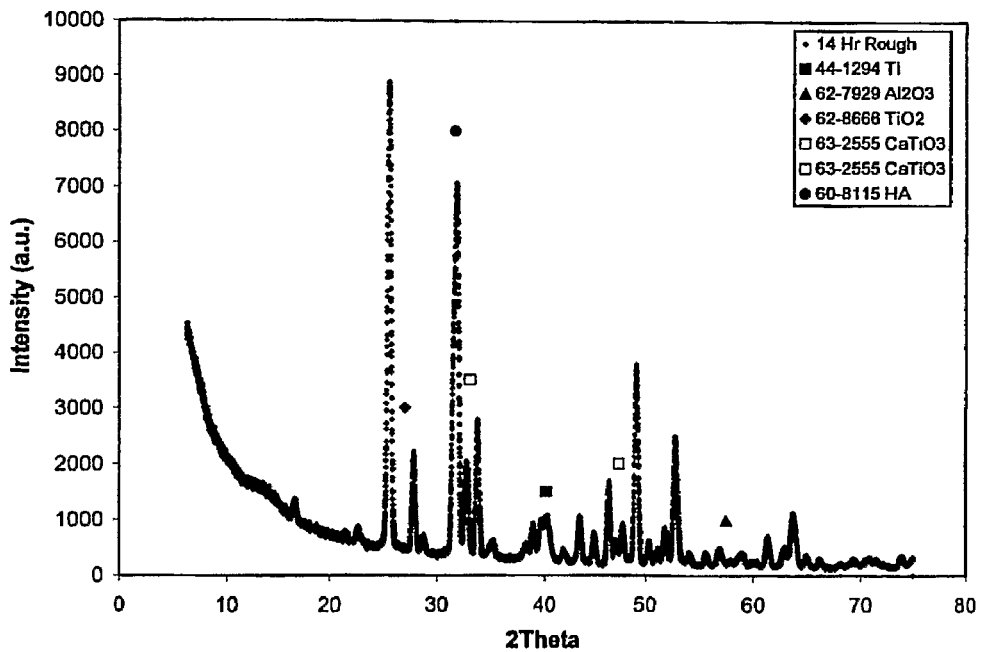
FIG. 21*a* is an XRD pattern of a hydroxyapatite coating after 14 hours.
Figure 21B:
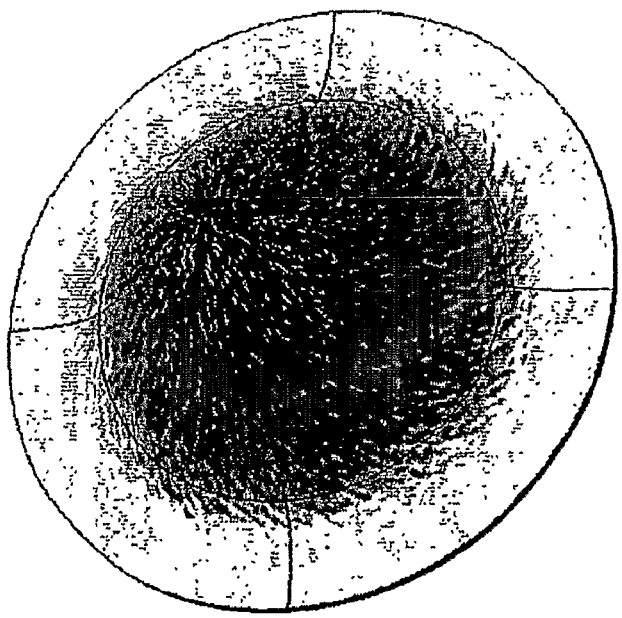
FIG. 21*b* is a pole figure of a hydroxyapatite coating after 14 hours.
Figure 22A:
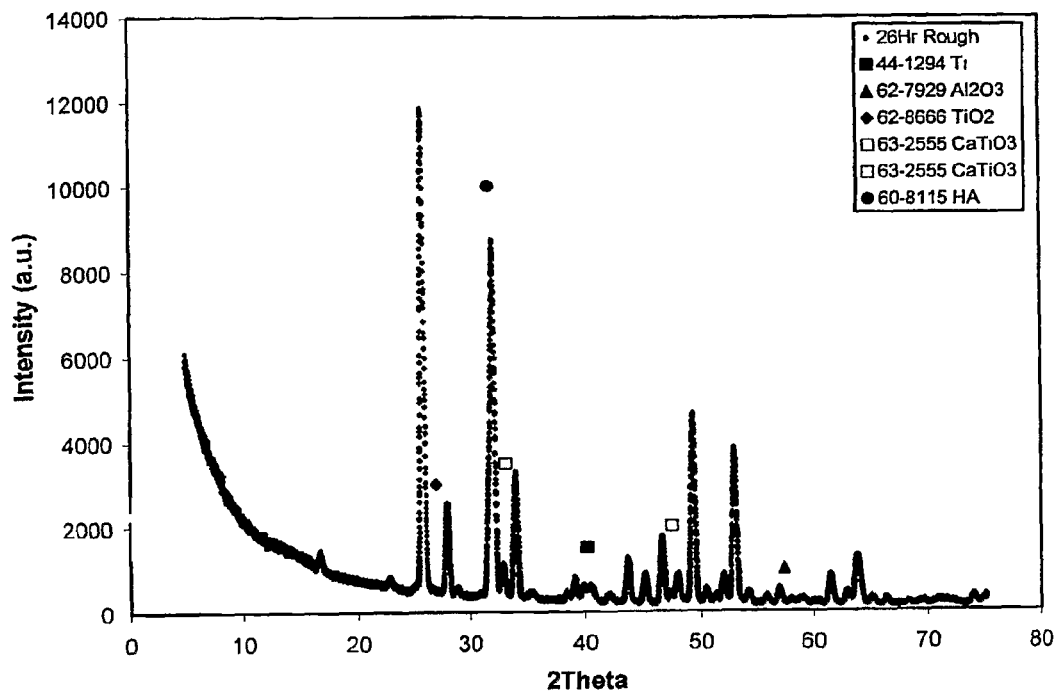
FIG. 22*a* is an XRD pattern of a hydroxyapatite coating after 26 hours.
Figure 22B:
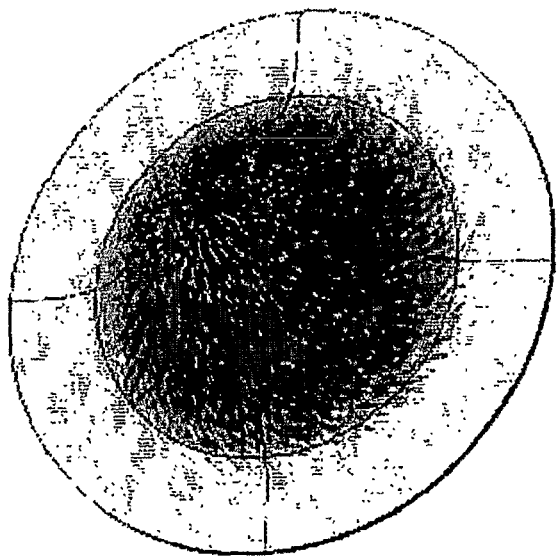
FIG. 22*b* is a pole figure of a hydroxyapatite coating after 26 hours.

FIG. 19 compares cell activity on textured and randomly oriented samples. For all data points up to nearly five weeks activity is increased on oriented samples as compared to randomly textured samples, including two points where activity is significantly greater. The most prominent difference between the two plots is the 3-4 day period where activity is flat on the randomly oriented substrate. This lag could be due to cells needing additional time to form a proper interface between themselves and the random coating because of differences in protein adhesion to the random surface versus the oriented surface. Regardless, if this is the exact explanation or not, this data illustrates for the first time in an applied system that crystal orientation has, at the very least, a small but significant affect on osteoblast bioactivity.

Osteoblast Mineralization

The ability of the hydroxyapatite coating to facilitate osteoblast differentiation, extracellular matrix product, and matrix mineralization was examined in multi-week cell culture.

A hydroxyapatite coated substrate synthesized for 18 hours was used for testing. MC3T3-E1 pre-osteoblast cells were seeded onto the coating. Two control wells were also seeded with cells. Cells were incubated and induced using 50 mg/mL ascorbic acid and 10 mm beta-glycerol-phosphate in cell media after 3 days in culture. On day 24, the FBS was changed due to a lack of mineralization in control samples. Controls were found to stain positive for alizarin red, a dye used to confirm mineralization, on day 48. On day 48, the HA coated sample was fixed and prepared for examination by SEM. Mineralization was also monitored using a second cell line, CK17 passage 8 OPN –/– pre-osteoblast cells using a coated sample synthesized for 18 hours. An identical procedure was used except D-MEM media was used and the cells were first induced after 7 days. Controls were found to stain positive for alizarin red on day 24. The experiment was ended after 24 days, 17 days after induction.

Mineralization and therefore normal cell differentiation was concluded to successfully have occurred on two different coating samples using two different osteoblast cell lines MC3T3-E1 and CK17. In each case, controls stained positive for mineral as well. FIGS. 20a-d show SEM micrographs of the sample plated with MC3T3-E1 cells after 48 days of incubation (45 days post induction). It can be seen that the cells and their matrix have filled in all the surface topography of the sample.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A film comprising phase-pure crystalline hydroxyapatite grains comprising a morphology selected from the group consisting of hexagons with a length from about 50 nm to about 5000 nm and an aspect ratio from about 0.5 to about 5; spheres comprising hexagonal primary particles and having a secondary particle size from about 50 nm to about 5000 nm; hollowed out tubular particles with a length from about 50 nm to about 5000 nm with an aspect ratio from about 0.5 to about 5; barrel-shaped particles with a length from about 50 nm to about 5000 nm with aspect ratio from about 0.5 to about 5.0; and mixtures thereof.

2. The film according to claim 1, further comprising a substrate over the surface of which said film is coated, wherein said substrate surface comprises a material selected from the group consisting of metals, metal oxides, alloys, and polymers stable in alkaline media at elevated temperature.

3. The film according to claim 2, wherein the metal comprises titanium.

4. The film according to claim 2, wherein the alloy comprises mild steel, stainless steel, cobalt/chrome, or a titanium alloy.

5. The film according to claim 2, wherein the polymer stable in alkaline media at elevated temperature comprises fluoropolymers, polyvinylchloride, or polyethylene terephtalate.

6. The film according to claim 2, wherein the substrate is selected from the group consisting of porous substrates, wire meshes, wires, rods, bars, ingots, sheets, and free-form shapes.

7. The film according to claim 6, wherein the substrate is selected from the group consisting of titanium, titanium alloy, steel, stainless steel, and cobalt-chrome.

8. The film according to claim 2, wherein the crystalline hydroxyapatite grains are oriented in essentially the same crystallographic orientation on the substrate.

9. The film according to claim 8, wherein the crystalline hydroxyapatite grains have varying lengths.

10. The film according to claim 2, wherein the texture of the film is smooth or rough.

11. The film according to claim 2, wherein the morphology is hexagonal and the substrate is a sapphire single crystal.

12. The film according to claim 2, wherein the morphology is cube-shaped and the substrate is zirconia.

13. The film according to claim 2, wherein at least a portion of said film comprises a passivation film.

14. The film according to claim 7 having a hexagon morphology.

15. A biocompatible hard tissue implant comprising the film according to claim 1.

16. The biocompatible hard tissue implant according to claim 15 comprising a metal or polymeric implant coated with said film.

17. The biocompatible hard tissue implant of claim 15 comprising a polymeric composite.

18. A ceramic powder comprising non-agglomerated non-aggregated phase-pure hydroxyapatite comprising a morphology selected from the group consisting of hexagons with a length from about 50 nm to about 5000 nm and an aspect ratio from about 0.5 to about 5; spheres comprising hexagonal primary particles and having a secondary particle size from about 50 nm to about 5000 nm; hollowed out tubular particles with a length from about 50 nm to about 5000 nm with an aspect ratio from about 0.5 to about 5; truncated ellipsoidal particles with a length from about 50 nm to about 5000 nm with aspect ratio from about 0.5 to about 5.0; and mixtures thereof.

19. A composite comprising a polymer and the ceramic powder according to claim 18.

20. The composite of claim 19, wherein the polymer is selected from the group consisting of poly-lactic acid, poly glycolic acid, polycaprolactone, copolymers thereof, and mixtures thereof.

21. A packing material for use in a chromatography column or gas sensor or as a catalytic support comprising the ceramic powder according to claim 18.

22. Aerosol particles comprising the ceramic powder according to claim 18.

23. An extending pigment for paints, coatings, and plastics comprising the ceramic powder according to claim 18.

24. A granular fill for direct incorporation into human or animal tissues comprising the ceramic powder according to claim 18.

25. The granular fill according to claim 24, comprising a metal or polymeric composite for filling dental cavities.

26. A dentifrice composition comprising the ceramic powder according to claim 18.

27. A method for producing a phase-pure hydroxyapatite comprising:
   a. dissolving a source of calcium ions, a source of hydroxide ions, and an organophosphate in a common solvent; and
   b. heating the solution at a temperature less than 300° C., so that the organophosphate hydrolyzes to form $PO_4^{3-}$ ions that react with said calcium and hydroxide ion sources to form hydroxyapatite of uniform size and morphology.

28. The method according to claim 27, wherein said calcium ion source comprises calcium ions bound to a chelating agent.

29. The method according to claim 28, wherein the chelating agent is ethylendiamine tetracetic acid (EDTA).

30. The method according to claim 27, wherein the solvent comprises water; and the hydroxide ion source comprises ammonia.

31. A method for producing a phase-pure hydroxyapatite film on a substrate comprising:
   a. dissolving a chelated source of calcium ions, a source of hydroxide ions, and an organophosphate in a common solvent;
   b. placing a substrate into the solution; and
   c. heating the solution at a temperature less than 300° C., so that the organophosphate hydrolyzes to form $PO_4^{3-}$ ions that react with said calcium and hydroxide ion sources to deposit hydroxyapatite on said substrate.

32. The method according to claim 27, wherein the organophosphate has a general formula $(RO)_3PO$, wherein R represents hydrogen or an organic hydrocarbon radical hydrolysis derivative of the organophosphate, provided that at least one R is not H.

33. The method according to claim 27, wherein the solubility of the organophosphate in water is not less than 5% by weight at room temperature.

34. The method according to claim 33, wherein the organophosphate is miscible with water at room temperature.

35. The method according to claim 31, wherein the calcium ions are chelated to a chelating agent selected from the group consisting of ethylene diaminetetracetic acid, a salt thereof, and mixtures thereof.

36. The method according to claim 31, wherein the temperature to which said solution is heated is selected to determine the crystallographic orientation, surface shape, or both, of the film.

37. The method according to claim 31, wherein said substrate is selected from the group consisting of metals, metal oxides, alloys, and polymers stable in alkaline media at elevated temperatures.

38. The method according to claim 37, wherein the metal comprises titanium.

39. The method according to claim 37, wherein the alloy comprises mild steel, stainless steel, cobalt/chrome, or a titanium alloy.

40. The method according to claim 27, wherein said solution is heated in a sealed vessel so that said reaction occurs at autogenous pressure.

41. The method according to claim 31, wherein the organophosphate has a general formula $(RO)_3PO$, wherein R represents hydrogen or an organic hydrocarbon radical hydrolysis derivative of the organophosphate, provided that at least one R is not H.

42. The method according to claim 31, wherein the solubility of the organophosphate in water is not less than 5% by weight at room temperature.

43. The method according to claim 31, wherein said solution is heated in a sealed vessel so that said reaction occurs at autogenous pressure.

* * * * *